US010399858B2

(12) United States Patent
Dusselier et al.

(10) Patent No.: US 10,399,858 B2
(45) Date of Patent: Sep. 3, 2019

(54) PRODUCING ZEOLITE SSZ-39 USING ISOMERIC MIXTURES OF ORGANIC STRUCTURE DIRECTING AGENTS

(71) Applicant: CALIFORNIA INSTITUTE OF TECHNOLOGY, Pasadena, CA (US)

(72) Inventors: Michiel J. Dusselier, Pasadena, CA (US); Mark E. Davis, Pasadena, CA (US); Joel E. Schmidt, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 317 days.

(21) Appl. No.: 14/929,571

(22) Filed: Nov. 2, 2015

(65) Prior Publication Data

US 2016/0122192 A1    May 5, 2016

Related U.S. Application Data

(60) Provisional application No. 62/074,484, filed on Nov. 3, 2014, provisional application No. 62/118,105, filed on Feb. 19, 2015.

(51) Int. Cl.
| | |
|---|---|
| *C01B 39/04* | (2006.01) |
| *C07C 1/20* | (2006.01) |
| *C07C 67/37* | (2006.01) |
| *C01B 39/48* | (2006.01) |
| *B01J 29/70* | (2006.01) |
| *B01J 35/00* | (2006.01) |
| *B01D 53/02* | (2006.01) |
| *B01D 53/94* | (2006.01) |

(52) U.S. Cl.
CPC .............. *C01B 39/04* (2013.01); *B01J 29/70* (2013.01); *B01J 35/002* (2013.01); *C01B 39/48* (2013.01); *C07C 1/20* (2013.01); *C07C 67/37* (2013.01); *B01D 53/02* (2013.01); *B01D 53/9409* (2013.01); *B01D 2253/108* (2013.01); *B01D 2255/2092* (2013.01); *B01D 2255/20707* (2013.01); *B01D 2255/20715* (2013.01); *B01D 2255/20738* (2013.01); *B01D 2255/50* (2013.01); *B01D 2255/9205* (2013.01); *B01J 2229/186* (2013.01); *B01J 2229/37* (2013.01); *C07C 2529/70* (2013.01)

(58) Field of Classification Search
None
See application file for complete search history.

(56) References Cited

U.S. PATENT DOCUMENTS

| | | | |
|---|---|---|---|
| 5,958,370 A † | 9/1999 | Zones | |
| 7,008,610 B2 † | 3/2006 | Cao | |
| 7,094,389 B2 † | 8/2006 | Cao | |
| 8,415,518 B2 * | 4/2013 | Hall | B01J 29/70 585/329 |
| 2005/0154244 A1 | 7/2005 | Cao et al. | |
| 2005/0197519 A1 | 9/2005 | Cao et al. | |
| 2015/0118150 A1 † | 4/2015 | Yang | |
| 2016/0144347 A1 * | 5/2016 | Sano | B01D 53/8628 423/700 |

FOREIGN PATENT DOCUMENTS

| | | | | |
|---|---|---|---|---|
| JP | PCT/JP2014/068264 | * | 7/2014 | ............. B01J 29/85 |
| WO | WO 1999/008961 A1 | | 2/1999 | |
| WO | WO 2005/063624 | | 7/2005 | |
| WO | WO 2008/016423 A1 | | 2/2008 | |

OTHER PUBLICATIONS

Tsuda et al. (Table I, Chem. Pharm. Bull, 18(12), 2499-2566 (Year: 1970).*
Booth et al. Journal of the Chemical Society, Perkin Transactions 2: Physical Organic Chemistry (1972-1999), 9. 899-907 (Year: 1978).*
Dusselier et al., "Influence of Organic Structure Directing Agent Isomer Distribution on the Synthesis of SSZ-39," Chemistry of Materials, Mar. 30, 2015, vol. 27, 2695-2702.
Tsuda et al., "Catalytic Hydrogenation of Dimethylpyridine Methiodides and Stereochemistry of Hydrogenation Products," Chemical and Pharmaceutical Bulletin, 1970, vol. 18(12), 2499-2506.
IZA-Structure-Commission, "Database of Zeolite Structures" http://izasc.biw.kuleuven.be/fmi/xsl/IZA-SC/ft.xsl, Accessed Jan. 7, 2016, 1 pg.
Martin, et al., "Efficient Synthesis of the Cu-SSZ-39 Catalyst for DeNOx Applications", Royal Society of Chemistry Journal, Jan. 2012, 4 pgs.
Martin, et al., "Efficient Synthesis of the Cu-SSZ-39 Catalyst for DeNOx Applications (Electronic Supplementary Information)" Royal Society of Chemistry Journal, 2015, 10 pgs.
Moliner, et al., "Cu-SSZ-39, an Active and Hydrothermally Stable Catalyst for the Selective Catalytic Reduction of $NO_x$,", Chem. Commun., 2012, 48(66), 8264-8266.
Tsuiji, et al., "Synthesis of 4,4'-trimethylenebis(1-benzyl-1-methylpiperidinium) diastereomers and their use as structure-directing agents in pure-silica molecular sieve syntheses", Microporous and Mesoporous Materials, 28(3), May 1999, 519-530.
Booth et al., "The Thermal Decomposition of Quaternary Ammonium Hydroxides. Part 5. The Importance of Conformational Factors in β-Eliminations from Quaternary Hydroxides derived from Piperidines, Morpholines, and Decahydroquinolines", J.C.S. Perkin II, Dec. 1978, 899-907.
Moliner et al., "Cu-SSZ-39, an active and hydrothermally stable catalyst for the selective catalytic reduction of NOx", Chem. Commun., 2012, 48, 8264-8266.
Moliner et al., "Electronic Supplementary Information (ESI)-Cu-SSZ-39, an active and hydrothermally stable catalyst for the selective catalytic reduction of NOx", The Royal Society of Chemistry, 2012, 11 pages.
Tsuda et al., "Catalytic Hydrogenation of Dimethylpyridine Methiodides and Stereochemistry of Hydrogenation Products", Chem. Pharm. Bull., 1970, 18(12), 2499-2506.

(Continued)

*Primary Examiner* — Yun Qian
(74) *Attorney, Agent, or Firm* — BakerHostetler

(57) ABSTRACT

The present disclosure is directed to producing zeolite structures, especially Zeolite SSZ-39, using organic structure directing agents (OSDAs). In particular, the OSDAs comprise isomeric mixtures of N,N-dialkyl piperidinium cations.

25 Claims, 15 Drawing Sheets

(56) References Cited

OTHER PUBLICATIONS

Wagner et al., "Guest/Host Relationships in the Synthesis of the Novel Cage-Based Zeolites SSZ-35, SSZ-36, and SSZ-39", J. Am. Chem. Soc., 2000, 122, 263-273.

Wagner, "Supplementary Data: Synthesis of Guest Molecules", J. Am. Chem. Soc., 1999, 16 pages.

Wagner et al., "Guest Relationship in the Synthesis of the Novel Cage-Based Zeolites SSZ-35, SSZ-36, and SSZ-39", J. AM. Chem. Soc., Dec. 1999, 122(2), 263-273.†

\* cited by examiner
† cited by third party

*2,6-dimethyl-piperidine based SDAs*

*3,5-dimethyl-piperidine based SDA*

*2-ethyl-piperidine based SDAs*

*other claimed SDAs*

*d6r (t-hpr)*

PRODUCING ZEOLITE SSZ-39 USING ISOMERIC MIXTURES OF ORGANIC STRUCTURE DIRECTING AGENTS

CROSS REFERENCE TO RELATED APPLICATIONS

This applications claims priority to U.S. Patent Application Ser. Nos. 62/074,484, filed Nov. 3, 2014 and 62/118,105, filed Feb. 19, 2015, the contents of each of which are incorporated by reference herein in their entireties for all purposes.

TECHNICAL FIELD

The present disclosure is directed to producing zeolite structures, especially Zeolite SSZ-39, using organic structure directing agents (OSDAs).

BACKGROUND

Microporous materials are of commercial interest in catalysis, adsorption and ion-exchange. Due to active site confinement, high surface areas and robust hydrothermal stability, these materials often display enhanced and advantageous properties. Lately, there has been increasing interest in materials that incorporate 8 membered T-atom rings (8MRs) in their structure for catalytic applications. Both silicoaluminophosphate (SAPO) and aluminosilicate (zeolite) compositions are of interest in this context. The two most prominent catalytic applications of 8MR molecular sieves are the methanol-to-olefins reaction (MTO) and the selective catalytic reduction (SCR) of NOx in flue and exhaust gases. SAPO-34, a material that has the CHA topology, is commercially applied in MTO, while its aluminosilicate analogue, Zeolites are more attractive catalysts in general, compared to SAPOs, because of a variety of properties including their higher (hydro)thermal stability and stronger acidity. This preference is reflected in their dominant presence in refining processes and petrochemistry. Given the similar topological needs for both MTO and deNOx, it could be beneficial if one zeolite could be made into an efficient catalyst for both applications. So far, few zeolite compositions that are highly active for MTO are efficient for deNOx or vice versa, the problem being the difference in optimal Si/Al ratios for both applications. DeNOx ideally operates on zeolites with low Si/Al molar ratios (<20), in order to achieve high active site (ion-exchanged Cu) loadings, whereas MTO is usually run with Si/Al ratios of over 20, owing to the increased deactivation and poor selectivities on zeolites with high Al content.

Promising 8MR materials include LEV, AFX, KFI, RTH and AEI framework topologies. The cage size and pore dimensionality are critical to the catalytic performance and stability of these materials. The AEI molecular sieve topology, in particular, describes a microporous material where the 8MRs constitute a 3D channel system (8×8×8) with equal pore sizes of 3.8×3.8 Å and medium size cages that can include spheres up to 7.3 Å. AEI molecular sieves display unique activity and selectivity patterns in MTO (e.g., H-SAPO-18 or zeolite H-SSZ-39) and, when exchanged with $Cu^{2+}$, in SCR. Moreover, the stability of the SSZ-39 zeolite is found high compared to the industrial standard 8MR zeolite (SSZ-13). Collectively, these reports suggest that SSZ-39 is a likely candidate for large-scale applications provided that the material can be synthesized efficiently. The latter is a common bottleneck hindering the exploitation of many unique zeolite topologies.

The present invention is directed to allowing an expanded range of OSDAs for use in preparing some of these materials as well as solving some of these shortcomings.

SUMMARY

The present invention is directed to the use of mixed isomers for use in the synthesis of aluminosilicate molecular sieve (zeolite) with the AEI framework topology (SSZ-39). In some embodiments, mixtures of the isomers of dimethylpiperidine-based organic structure directing agents (OSDAs) are shown to be useful for preparing SSZ-39. The influence of diastereo- and structural isomeric mixtures on the synthesis of SSZ-39 is disclosed. Although differences in the rates of molecule sieve formation and the preferential incorporation of isomers occur, the synthesis of SSZ-39 is possible over a wide range of isomeric mixtures.

Certain embodiments of the present invention include those processes comprising hydrothermally treating a composition comprising
 (a) at least one source of silicon oxide, germanium oxide, or a combination thereof;
 (b) water; and
 (c) an organic structure directing agent mixture comprising at least two isomers of the quaternary piperidinium cation of Formula (I):

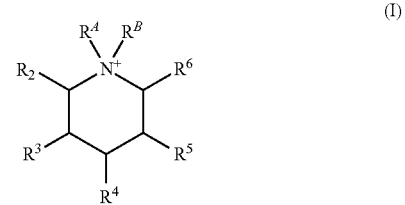

(I)

under conditions effective to crystallize a crystalline composition having an AEI framework topology; wherein
 $R^A$ and $R^B$ are independently a $C_{1-3}$ alkyl, or together with the N to which they are bound form a 5 or 6 membered saturated or unsaturated ring; and
 $R^2$, $R^3$, $R^4$, $R^5$, and $R^6$ are independently H or $C_{1-3}$ alkyl, provided at least two of $R^2$, $R^3$, $R^4$, $R^5$, and $R^6$ are independently $C_{1-3}$ alkyl.

The presence of sources of silicon oxide, either by themselves or in combination with sources of germanium is preferred.

In some of these embodiments, the composition further comprises at least one source of aluminum oxide, boron oxide, gallium oxide, hafnium oxide, iron oxide, tin oxide, titanium oxide, indium oxide, vanadium oxide, zirconium oxide, or a combination thereof.

The presence of sources of aluminum oxide, either by themselves or in combination with sources of any of these other oxides is preferred.

In some of these embodiments, $R^2=R^4=R^6=H$. $R^3$ and $R^5$ may be methyl.

In other embodiments $R^3=R^4=R^5=H$. $R^2$ and $R^6$ may be methyl.

In some embodiments, $R^A$ and $R^B$ are independently a $C_{1-3}$ alkyl, preferably methyl or ethyl, more preferably methyl. $R^A$ and $R^B$, together with the N to which they are bound, may also form a structure of a form:

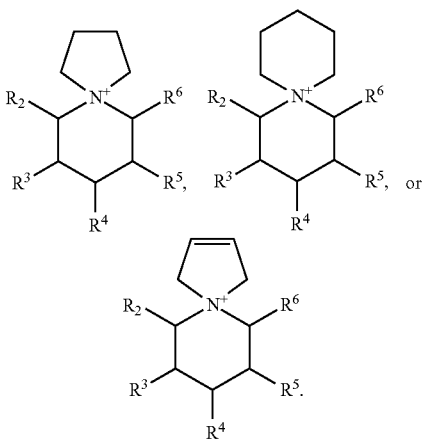

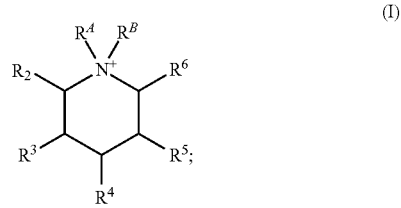

The at least two isomers of the quaternary piperidinium cation of Formula (I) may be structural isomers of one another, stereo-isomers of one another, or a combination thereof. Exemplary structures include N,N-dimethyl-3,5-lupetidinium cation, N,N-dimethyl-2,6-lupetidinium cation, or a combination thereof, or mixtures of cis-N,N-dimethyl-3,5-lupetidinium cation and trans-N,N-dimethyl-3,5-lupetidinium cation, a mixture of cis-N,N-dimethyl-2,6-lupetidinium cation and trans-N,N-dimethyl-3,5-lupetidinium cation, or a combination thereof. Where present as stereoisomers, the ratios may range from 95% cis/10% trans to about 10% cis/95% trans. Typically, but not necessarily, the organic structure directing agent mixture comprises a hydroxide salt of the at least two isomers of the quaternary piperidinium cation of Formula (I).

The source of silicon oxide may comprise a silicate, silica hydrogel, silicic acid, fumed silica, colloidal silica, tetra-alkyl orthosilicate, a silica hydroxide or combination thereof. The sources of germanium oxide include hydroxides, oxyhydroxides, alkoxides, or carboxylates of germanium. The sources of aluminum oxide may comprise an alkoxide, hydroxide, or oxide of aluminum, a sodium aluminate, an aluminum siloxide, or combination thereof. The sources of boron oxide, gallium oxide, germanium oxide, hafnium oxide, iron oxide, tin oxide, titanium oxide, indium oxide, vanadium oxide, zirconium oxide, or combination or mixture thereof may comprise an alkoxide, hydroxide, oxide, or combination thereof of the corresponding oxide.

In some embodiments, the hydrotreated composition further comprises aqueous hydroxide.

The hydrothermally treating is typically done at one or more temperature in a range of from about 100° C. to about 200° C. for a time effective for crystallizing the crystalline microporous solid. These crystalline microporous solids may be isolated. The crystalline microporous solids may further be calcined at one or more temperatures in a range of from about 350° C. to about 850° C. The calcined material may further be treated with an aqueous ammonium salt, with at least one type of alkaline earth or transition metal or metal oxide. In some embodiments, the at least one type of transition metal or transition metal oxide comprises cobalt, copper, iron, or a mixture thereof.

Other embodiments include those compositions which may be formed or present during the methods described herein. For example, some embodiments provide compositions comprising:

(a) at least one source of silicon oxide, germanium oxide, or a combination thereof;

(b) water;

(c) an organic structure directing agent mixture comprising at least two isomers of the quaternary piperidinium cation of Formula (I):

and (d) a compositionally consistent crystalline microporous solid of an AEI framework;

wherein:

$R^A$ and $R^B$ are independently a $C_{1-3}$ alkyl, or together with the N to which they are bound form a 5 or 6 membered saturated or unsaturated ring; and $R^2$, $R^3$, $R^4$, $R^5$, and $R^6$ are independently H or $C_{1-3}$ alkyl, provided at least two of $R^2$, $R^3$, $R^4$, $R^5$, and $R^6$ are independently $C_{1-3}$ alkyl.

In other embodiments, the compositions further comprise at least one source of aluminum oxide, boron oxide, gallium oxide, hafnium oxide, iron oxide, tin oxide, titanium oxide, indium oxide, vanadium oxide, zirconium oxide, or a combination thereof.

In such compositions, the crystalline microporous solid may contain a portion of the one or both of the at least two isomers of the quaternary piperidinium cation of Formula (I).

These compositions may further comprise aqueous hydroxide. The composition may be in the form of a gel In some embodiments, the crystalline materials may be isolated, calcined, and post-treated as conventionally known in this field of study.

The invention also contemplates that the crystalline compositions are also useful in the catalysis of a number of organic transformations, at least one of which is the transformation of methanol to at least one type of olefin.

BRIEF DESCRIPTION OF THE DRAWINGS

The present application is further understood when read in conjunction with the appended drawings. For the purpose of illustrating the subject matter, there are shown in the drawings exemplary embodiments of the subject matter; however, the presently disclosed subject matter is not limited to the specific methods of making and methods of using, processes, devices, and systems disclosed. In addition, the drawings are not necessarily drawn to scale. In the drawings.

DETAILED DESCRIPTION OF ILLUSTRATIVE EMBODIMENTS

The present invention is directed to preparing microporous crystalline compositions of AEI topologies, for example SSZ-39 using isomeric mixtures (both structural and stereochemical isomers) of piperidinium based Organic Structure Directing Agents (OSDAs), and corresponding compositions.

Figure 1:
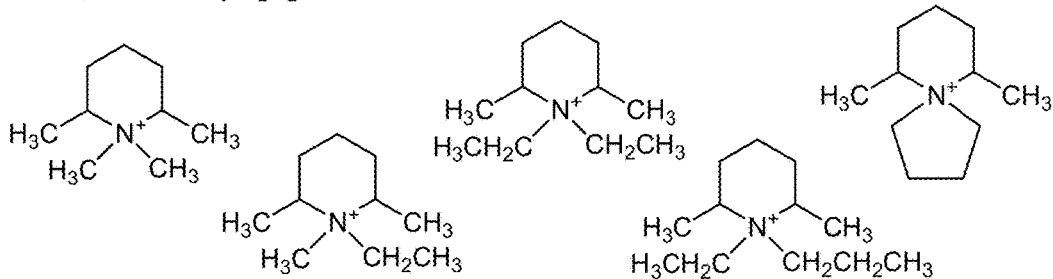
FIG. 1 shows an array of organic SDAs used previously for SSZ-39 synthesis.
Figure 1:
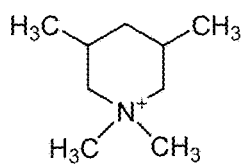
Figure 1:
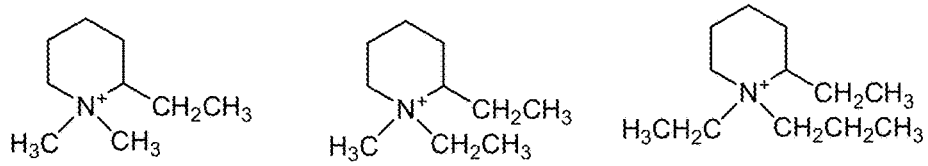
Figure 1:
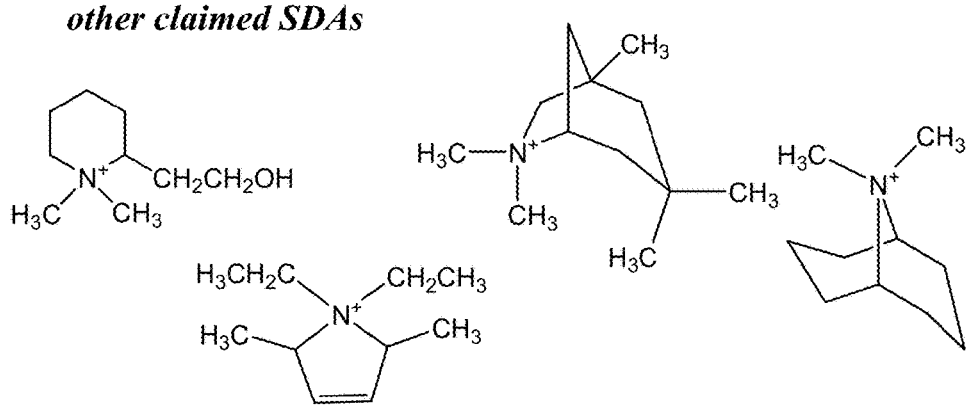
Figure 2A:
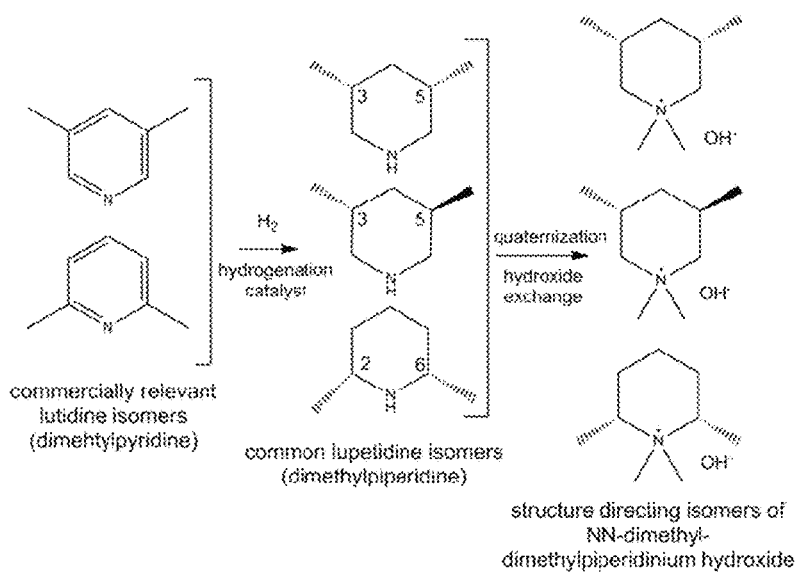
FIGS. 2A-B show options for organic mixtures of isomers of lupetidine, their origin from lutidines and the OSDAs made by amine quaternization and hydroxide exchange.
Figure 2B:
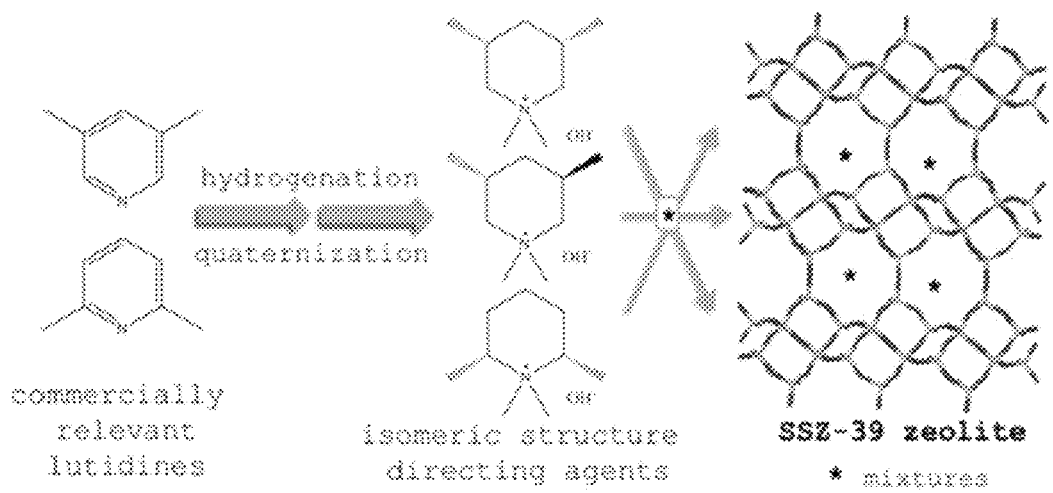

SSZ-39 has been synthesized using a variety of ODSAs (see FIG. 1). Some of the proposed OSDAs share a common feature in their chemical structure, namely, the dimethylpiperidine (lupetidine) moiety (viz. FIG. 2: N,N-diethyl or dimethyl quaternized lupetidines are OSDAs for SSZ-39). From an economic point of view, especially the 3,5- and 2,6-lupetidines are of interest, since their respective pyridine precursors, known as lutidines (FIG. 2), are among the most common, commercially produced alkylpyridines, serving as precursors to drugs and specialty chemicals. The hydrogenation procedure (and especially the catalyst) used to convert the lutidines determines the stereochemistry of the lupetidine products. Usually, a mixture of cis and trans-3, 5-lupetidine within a compositional range of 25:75 up to 100:0 (cis:trans) is obtained; whereas for the 2,6-isomer, the cis-form dominates in the product mixture, likely due to an increased steric hindrance in producing the trans variety. Significant economic advantages may be achievable if a mixture of two or more of these organic isomers could be used to synthesize SSZ-39. This would align the synthesis of SSZ-39 with the current lutidine synthesis and hydrogenation selectivities.

The present invention may be understood more readily by reference to the following description taken in connection with the accompanying Figures and Examples, all of which form a part of this disclosure. It is to be understood that this invention is not limited to the specific products, methods, processes, conditions or parameters described or shown herein, and that the terminology used herein is for the purpose of describing particular embodiments by way of example only and is not intended to be limiting of any claimed invention. Similarly, unless specifically otherwise stated, any description as to a possible mechanism or mode of action or reason for improvement is meant to be illustrative only, and the invention herein is not to be constrained by the correctness or incorrectness of any such suggested mechanism or mode of action or reason for improvement. Throughout this specification, claims, and drawings, it is recognized that the descriptions refer to compositions and processes of making and using said compositions. That is, where the disclosure describes or claims a feature or embodiment associated with a composition or a method of making or using a composition, it is appreciated that such a description or claim is intended to extend these features or embodiment to embodiments in each of these contexts (i.e., compositions, methods of making, and methods of using).

Terms

In the present disclosure the singular forms "a," "an," and "the" include the plural reference, and reference to a particular numerical value includes at least that particular value, unless the context clearly indicates otherwise. Thus, for example, a reference to "a material" is a reference to at least one of such materials and equivalents thereof known to those skilled in the art, and so forth.

When a value is expressed as an approximation by use of the descriptor "about," it will be understood that the particular value forms another embodiment. In general, use of the term "about" indicates approximations that can vary depending on the desired properties sought to be obtained by the disclosed subject matter and is to be interpreted in the specific context in which it is used, based on its function. The person skilled in the art will be able to interpret this as a matter of routine. In some cases, the number of significant figures used for a particular value may be one non-limiting method of determining the extent of the word "about." In other cases, the gradations used in a series of values may be used to determine the intended range available to the term "about" for each value. Where present, all ranges are inclusive and combinable. That is, references to values stated in ranges include every value within that range.

It is to be appreciated that certain features of the invention which are, for clarity, described herein in the context of separate embodiments, may also be provided in combination in a single embodiment. That is, unless obviously incompatible or specifically excluded, each individual embodiment is deemed to be combinable with any other embodiment(s) and such a combination is considered to be another embodiment. Conversely, various features of the invention that are, for brevity, described in the context of a single embodiment, may also be provided separately or in any sub-combination. Finally, while an embodiment may be described as part of a series of steps or part of a more general structure, each said step may also be considered an independent embodiment in itself, combinable with others.

The transitional terms "comprising," "consisting essentially of," and "consisting" are intended to connote their generally in accepted meanings in the patent vernacular; that is, (i) "comprising," which is synonymous with "including," "containing," or "characterized by," is inclusive or open-ended and does not exclude additional, unrecited elements or method or process steps; (ii) "consisting of" excludes any element, step, or ingredient not specified in the claim; and (iii) "consisting essentially of" limits the scope of a claim to the specified materials or steps "and those that do not materially affect the basic and novel characteristic(s)" of the claimed invention. Embodiments described in terms of the phrase "comprising" (or its equivalents), also provide, as embodiments, those which are independently described in terms of "consisting of" and "consisting essentially of" For those embodiments provided in terms of "consisting essentially of," the basic and novel characteristic(s) of a process is the ability to provide a SSZ-39 zeolite using mixtures, including isomeric mixtures, of OSDAs.

When a list is presented, unless stated otherwise, it is to be understood that each individual element of that list, and every combination of that list, is a separate embodiment. For example, a list of embodiments presented as "A, B, or C" is to be interpreted as including the embodiments, "A," "B," "C," "A or B," "A or C," "B or C," or "A, B, or C."

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are described herein.

Unless otherwise stated, ratios or percentages are intended to refer to mole percent or atom percent, as appropriate.

Throughout this specification, words are to be afforded their normal meaning, as would be understood by those skilled in the relevant art. However, so as to avoid misunderstanding, the meanings of certain terms will be specifically defined or clarified.

"Lower alcohols" or lower alkanes refer to alcohols or alkanes, respectively, having 1-10 carbons, linear or branched, preferably 1-6 carbon atoms and preferably linear. Methanol, ethanol, propanol, butanol, pentanol, and hexanol are examples of lower alcohols. Methane, ethane, propane, butane, pentane, and hexane are examples of lower alkanes.

The terms "separating" or "separated" carry their ordinary meaning as would be understood by the skilled artisan, insofar as they connote physically partitioning or isolating the product material from other starting materials or co-products or side-products (impurities) associated with the reaction conditions yielding the material. As such, it infers that the skilled artisan at least recognizes the existence of the product and takes specific action to separate or isolate it from starting materials and/or side- or byproducts. Absolute purity is not required, though it is preferred.

Unless otherwise indicated, the term "isolated" means physically separated from the other components so as to be free of at least solvents or other impurities, such as starting materials, co-products, or byproducts. In some embodiments, the isolated crystalline materials, for example, may be considered isolated when separated from the reaction mixture giving rise to their preparation, from mixed phase co-products, or both. In some of these embodiments, for example, pure SSZ-39 can be made directly from the described methods. In other cases, the formed SSZ-39 products form containing zeolites of GIS topology. GIS is a common impurity in synthesis from Al-rich gels, but it can be removed by a simple HCl-treatment that preserves the OSDA-stabilized SSZ-39. In some cases, it may not be possible to separate crystalline phases from one another, in which case, the term "isolated" can refer to separation from their source compositions.

"Optional" or "optionally" means that the subsequently described circumstance may or may not occur, so that the description includes embodiments where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present. Similarly, the phrase "optionally isolated" means that the target material may or may not be separated from other materials used or generated in the method, and, thus, the description includes separate embodiments where the target molecule or other material is separated and where the target material is not separated, such that subsequence steps are conducted on isolated or in situ generated product.

The terms "method(s)" and "process(es)" are considered interchangeable within this disclosure.

As used herein, the term "crystalline microporous solids" or "crystalline microporous silicate or aluminosilicate solids," sometimes referred to as "molecular sieves," are crystalline structures having very regular pore structures of molecular dimensions, i.e., under 2 nm. The term "molecular sieve" refers to the ability of the material to selectively sort molecules based primarily on a size exclusion process. The maximum size of the species that can enter the pores of a crystalline microporous solid is controlled by the dimensions of the channels. These are conventionally defined by the ring size of the aperture, where, for example, the term "8-MR" or "8-membered ring" refers to a closed loop that is typically built from eight tetrahedrally coordinated silicon (or aluminum) atoms and 8 oxygen atoms. These rings are not necessarily symmetrical, due to a variety of effects including strain induced by the bonding between units that are needed to produce the overall structure, or coordination of some of the oxygen atoms of the rings to cations within the structure. The term "silicate" refers to any composition including silica. It is a general term encompassing, for example, pure-silica, aluminosilicate, borosilicate, or titano-silicate structures. The term "zeolite" refers to an aluminosilicate composition that is a member of this family. When described as "optionally substituted," the zeolite framework may contain boron, gallium, hafnium, iron, tin, titanium, indium, vanadium, or zirconium atoms substituted for one or more aluminum or silicon atoms in the framework. SSZ-39 is a zeolite with the AEI framework. The intrazeolitic pore space of AEI consists of a three-dimensional interconnected channel system, bound by 8MR rings (3.8×3.8 Å) and basket-shaped cages.

The present disclosure describes and is intended to lay claim to methods of making crystalline compositions, the compositions themselves, and methods of using the crystalline compositions having an AEI framework, including those exhibiting the aluminosilicate SSZ-39 topology. As described elsewhere as well, it should be appreciated that any embodied feature described for one of these categories (i.e., compositions and methods of making or using) is applicable to all other categories.

Processes of Preparing Crystalline Compositions

Certain embodiments of the present invention include those processes comprising hydrothermally treating a composition comprising:
  (a) at least one source of silicon oxide, germanium oxide, or a combination thereof;
  (b) water; and
  (c) an organic structure directing agent mixture comprising at least two isomers of the quaternary piperidinium cation of Formula (I):

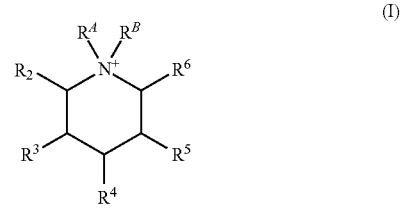

under conditions effective to crystallize a crystalline composition having an AEI framework topology;
  wherein
  $R^A$ and $R^B$ are independently a $C_{1-3}$ alkyl, or together with the N to which they are bound form a 5 or 6 membered saturated or unsaturated ring; and
  $R^2$, $R^3$, $R^4$, $R^5$, and $R^6$ are independently H or $C_{1-3}$ alkyl, provided at least one (i.e., one, two, three, four, or five) of $R^2$, $R^3$, $R^4$, $R^5$, and $R^6$ are independently $C_{1-3}$ alkyl.

As described herein, the as-formed and post-treated crystalline compositions themselves are independent embodiments of the present invention.

Similarly, the use of sources of silicon oxide, germanium oxide, and any combination thereof represent individual and independent embodiments. The presence of sources of silicon oxide, either by themselves or in combination with sources of germanium is preferred.

The sources of silicon oxide may include silicates, silica hydrogels, silicic acid, fumed silica, colloidal silica, tetraalkyl orthosilicates, silica hydroxide or combination thereof. Sodium silicate or tetraorthosilicates are preferred sources. Corresponding sources of germanium oxide can include alkali metal orthogermanates, $M_4GeO_4$, containing discrete $GeO_4^{4-}$ ions, $GeO(OH)_3^-$, $GeO_2(OH)_2^{2-}$, $[(Ge(OH)_4)_8(OH)_3]^{3-}$ or neutral solutions of germanium dioxide contain $Ge(OH)_4$, or alkoxide or carboxylate derivatives thereof.

In other embodiments, compositions of the present methods further comprises at least one source of aluminum oxide, boron oxide, gallium oxide, hafnium oxide, iron oxide, tin oxide, titanium oxide, indium oxide, vanadium oxide, zirconium oxide, or a combination thereof. Within this context, the use of sources of aluminum oxide, boron oxide, gallium oxide, hafnium oxide, iron oxide, tin oxide, titanium oxide, indium oxide, vanadium oxide, zirconium oxide, and any combination thereof represent individual and independent embodiments. The presence of sources of aluminum oxide, either by themselves or in combination with sources of any of these other oxides is preferred.

The source of aluminum oxide may comprise an alkoxide, hydroxide, or oxide of aluminum, a sodium aluminate, an aluminum siloxide, an aluminosilicate, or combination thereof. In some embodiments, a mesoporous or zeolite aluminosilicate material may be used as a source of both aluminum oxide and silicon oxide. For example, FAU type zeolites serve as useful precursors, for example in structures having Si/Al=2.6. In such circumstances, using sodium silicate or tetraorthosilicates for a source of additional silicon oxide also works well. Where other oxides are used, these may be derived from boron oxide, gallium oxide, germanium oxide, hafnium oxide, iron oxide, tin oxide, titanium oxide, indium oxide, vanadium oxide, zirconium oxide, or combination or mixture thereof, including materials comprising an alkoxide, hydroxide, oxide, or combination thereof of the corresponding metal.

In the presence of appropriate starting materials, the crystalline compositions having the AEI framework topology formed by these processes may be characterized as a zeolite SSZ-39 material.

The hydrothermal treating is typically done at a temperature in a range of from about 100° C. to about 200° C. for a time effective for crystallizing the crystalline microporous solid. Independent embodiments include those where the hydrothermal treating temperature is in at least one range of from about 100° C. to 120° C., from 120° C. to 140° C., from 140° C. to 160° C., from 160° C. to 180° C., from 180° C. to 200° C., or any combination of two or more of these ranges. These ranges provide for convenient reaction times, though higher and lower temperatures may also be employed. This hydrothermal treating is also typically done in a sealed autoclave, at autologous pressures. Some exemplary reaction conditions are provided in the Examples.

In these processes, the mole ratio of Si:Al in the composition is typically in a range of from about 5:1 to about 10:1, from 10:1 to 15:1, from 15:1 to 20:1, from 20:1 to 30:1, from 30:1 to 40:1, from 40:1 to 50:1, from 50:1 to 60:1, from 60:1 to 70:1, from 70:1 to 80:1, from 80:1 to 90:1, from 90:1 to 100:1, from 100:1 to 150:1, from 150:1 to 200:1, from 200:1 to 250:1, or any combination of two or more of these ranges, for example, from about 5:1 to about 250:1, from 10:1 to 100:1, from 15:1 to 30:1, or from 30:1 to 50:1. Again, the initial ratios of precursors will, at least in part, define the stoichiometries of the final crystalline materials. The person of skill in the art, using the teachings provided herein would be able to define the specific final stoichiometries of interest without undue experimentation. It should be appreciated that while these stoichiometries are defined solely in terms of Si and Al, some portion or all of the Si content may be substituted by Ge, and some portion of the Al may be substituted by B, Ga, Hf, Fe, Sn, Ti, In, V, or Zr.

In still further embodiments, the mole ratio of water to Si can be in a range of from about 2:1 to about 50:1, including ranges of from 2:1 to 5:1, from 5:1 to 10:1, from 10:1 to 15:1, from 15:1 to 20:1, from 20:1 to 30:1, from 30:1 to 40:1, from 40:1 to 50:1, or any combination of two or more of these ranges. Higher ratios, e.g., from 15:1 to 30:1, or about 28:1, may be preferred. Again, while described in terms of Si alone, in additional embodiments, these ratios may also refer to the presence of Si, Ge, or both.

The process may also be defined in terms of the mole ratio of the piperidinium cation to Si. In some of these embodiments, the mole ratio of the piperidinium cation to Si is in a range of from about 0.01:1 to about 1:1, including ranges of from 0.01 to 0.02:1, from 0.02:1 to 0.05:1, from 0.05:1 to 0.07:1, from 0.07:1 to 0.1:1, from 0.1:1 to 0.15:1, from 0.15:1 to 0.2:1, from 0.2:1 to 0.25:1, from 0.25:1 to 0.3:1, from 0.3:1 to 0.4:1, from 0.4:1 to 0.5:1, or any combination of two or more of these ranges, for example, from 0.01:1 to 1:1, from 0.02:1 to 0.5:1, or from 0.5:1 to 0:25:1. Again, while described in terms of Si alone, in additional embodiments, the reference to Si may also refer to the presence of Si, Ge, or both.

Typically, the composition being hydrothermally treated further comprises aqueous alkali metal or alkaline earth metal hydroxide, for example LiOH, NaOH, KOH, or $Ca(OH)_2$, thereby rendering these mixtures alkaline. In some cases, the pH of the water is in a range of from 7 to 7.5, from 7.5 to 8, from 8 to 8.5, from 8.5 to 9, from 9 to 9.5, from 9.5 to 10, from 10 to 11, from 11 to 12, from 12 to 13, from 13 to 14, or any combination of two or more of these ranges. Under these conditions, the oxide precursors can be expected to be at least partially hydrated to their hydroxide forms. In some embodiments, the mole ratio of hydroxide to Si (/Ge) in the composition may in a range of from about 0.5:1 to about 1:1, preferably 0.6:1 to 0.8:1. In some of these embodiments, the mole ratio of the hydroxide to Si is in a range of from about 0.4:1 to 0.45:1, from 0.45:1 to 0.5:1, from 0.5:1 to 0.55:1, from 0.55:1 to 0.6:1, from 0.6:1 to 0.65:1, from 0.65:1 to 0.7:1, from 0.7:1 to 0.75:1, from 0.75:1 to 0.8:1, or any combination of two or more of these ranges, with OH— being the sum of the added $OH^-$ and OSDA(OH—) contents. Depending on the amount of piperidinium cation used in the process, these amounts may be inclusive of any hydroxide anion associated with the compound of Formula (I).

While mixtures of any of the preceding ratio sets represent individual embodiments of the present invention, good results were achieved when the compositional range of the reaction mixture (preferably as a gel) was:

1 Si: 0.033-0.066 Al: 0.07-0.14 OSDA: 0.65-0.71 $OH^-$: 0.51-0.58 $Na^+$: 20-30$H_2O$, with OH— being the sum of the NaOH and OSDA(OH—) contents.

Turning next to the organic structure directing agent ("OSDA"), this is described in some embodiments as comprising at least two isomers of the quaternary piperidinium cation of Formula (I):

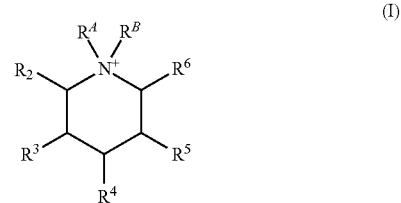

wherein
$R^A$ and $R^B$ are independently a $C_{1-3}$ alkyl, or together with the N to which they are bound form a 5 or 6 membered saturated or unsaturated ring; and
$R^2$, $R^3$, $R^4$, $R^5$, and $R^6$ are independently H or $C_{1-3}$ alkyl, provided at least one (i.e., one, two, three, four, or five) of $R^2$, $R^3$, $R^4$, $R^5$, and $R^6$ are independently $C_{1-3}$ alkyl.

The counterion to the cationic organic structure directing agent mixture is generally a bromide, chloride, fluoride, iodide, or hydroxide ion, preferably a hydroxide ion, but the OSDA may be added also to the composition as an acetate, nitrate, or sulfate.

The following descriptions provide options for any single isomer, but again, it should be appreciated that the instant invention provides that the OSDA comprises two or more different compounds, selected from these options. For the sake of brevity, reference to an isomer by individual digits is intended to refer to that isomer substituted in that position. For example, the "2,6 isomer" refers to an isomer containing an alkyl substituent only in the $R^2$ and $R^6$ positions; a "3,5 isomer" refers to an isomer containing an alkyl substituent only in the $R^3$ and $R^5$ positions.

In certain embodiments, each individual OSDA may comprise a compound in which at least two of $R^2$, $R^3$, $R^4$, $R^5$, and $R^6$ are independently $C_{1-3}$ alkyl. Such compounds include those individual options in which one, two, three, four, or five of $R^2$, $R^3$, $R^4$, $R^5$, and $R^6$ are independently $C_{1-3}$ alkyl are each considered independent embodiments. Moreover, reference to "isomers" in the term "at least two isomers of the quaternary piperidinium cation of Formula (I)" refers to both structural and stereochemical isomers. That is, the term "at least two isomers of the quaternary piperidinium cation of Formula (I)" may comprise multiple structural isomers (e.g., individual mono-alkyl compounds substituted in the 2, 3, 4, 5, or 6 positions, or dialkyl compounds substituted in the 2,3 and 2,4 and 2,5 and 2,6, and 3,4 and 3,5, and 4,5 positions, or combinations thereof). In some cases, these may include mixtures of homologs (e.g., where $R^2$ is methyl and $R^6$ is ethyl), stereoisomers of the same structural isomer (e.g., cis-2-methyl/6-methyl and trans-2-methyl/6-methyl), or combinations of both (e.g., cis-2-methyl/6-methyl and trans-2-methyl/6-ethyl).

For example, referring to the structure of Formula (I), options for the OSDA compounds include those where $R^2$, $R^3$, $R^4$, $R^5$, and $R^6$ are individually and independently methyl, ethyl, n-propyl, or iso-propyl, independent of stereochemistry. In separate embodiments, the carbon skeleton of piperidinium cation may be mono-, di-, tri-, tetra-, or penta-substituted with any of these $C_{1-3}$ alkyl groups, independent of stereochemistry.

The piperidine framework of these OSDAs may be conveniently derived from the hydrogenation of mono-, di-, tri, or tetraalkyl pyridine or pyridinium precursors, for example using $Pt/H_2$ or Raney Nickel catalysts. Given the availability of such pyridine or pyridinium precursors, in some embodiments, dialkyl piperidinium frameworks are conveniently obtained, especially, for example, where $R^3$ and $R^5$ are alkyl, preferably ethyl or methyl, more preferably methyl or where $R^2$ and $R^6$ are alkyl, preferably ethyl or methyl, more preferably methyl. In the former case, where $R^3$ and $R^5$ are methyl and $R^2$, $R^4$, and $R^6$ are H, the structures are known as 3,5-lupetidinium cations. In the latter case, where $R^2$ and $R^6$ are methyl and $R^3$, $R^4$, and $R^5$ are H, the structures are known as 2,6-lupetidinium cations.

$R^A$ and $R^B$ are defined as being independently a $C_{1-3}$ alkyl, or together with the N to which they are bound form a 5 or 6 membered saturated or unsaturated ring. As such, in some embodiments, $R^A$ and $R^B$ are independently methyl, ethyl, n-propyl, or iso-propyl. In other embodiments, $R^A$ and $R^B$, together with the N to which they are bound, form a 5 or 6 membered saturated or unsaturated ring. For example, these may include structures described as a spiro-pyrrolidinium moiety, also described as a 5-azonia-spiro[4,5]decane:

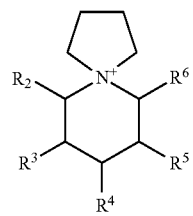

or a spiro-piperidinium moiety, also described as a 6-azonia-spiro[4,5]undecane:

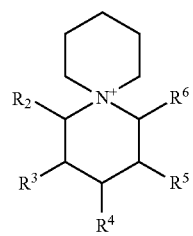

or a spiro-2,5-dihydro-1H-pyrrolium moiety, also described as a 5-azonia-spiro[4,5]dec-2-ene:

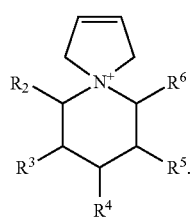

Again, in certain embodiments of these structures, the 2,6 positions (i.e., $R^2$ and $R^6$) are alkyl, preferably ethyl or methyl, more preferably methyl, the remaining positions being H. In other embodiments, the 3,5 positions (i.e., $R^3$ and $R^5$) are alkyl, preferably ethyl or methyl, more preferably methyl, the remaining positions being H.

Specific embodiments include those wherein the quaternary piperidinium cation of Formula (I) is an N,N-dialkyl-3,5-lupetidinium cation, N,N-dialkyl-2,6-lupetidinium cation, or a combination thereof. In this context, the reference to N,N-dialkyl may also include the 5-azonia-spiro[4,5]decane, 5-azonia-spiro[4,5]dec-2-ene, or 6-azonia-spiro[4,5]undecane derivatives described above.

In other embodiments, the quaternary piperidinium cation of Formula (I) is an N,N-dimethyl-3,5-lupetidinium cation, N,N-dimethyl-2,6-lupetidinium cation, N,N-diethyl-3,5-lupetidinium cation, N,N-diethyl-2,6-lupetidinium cation, a 6,10-dimethyl-5-azonia-spiro[4.5]decane, a 1,5-dimethyl-6-azonia-spiro[5.5]undecane, a 7,9-dimethyl-5-azonia-spiro[4.5]decane, a 2,4-dimethyl-6-azonia-spiro[5.5]undecane, or a combination thereof

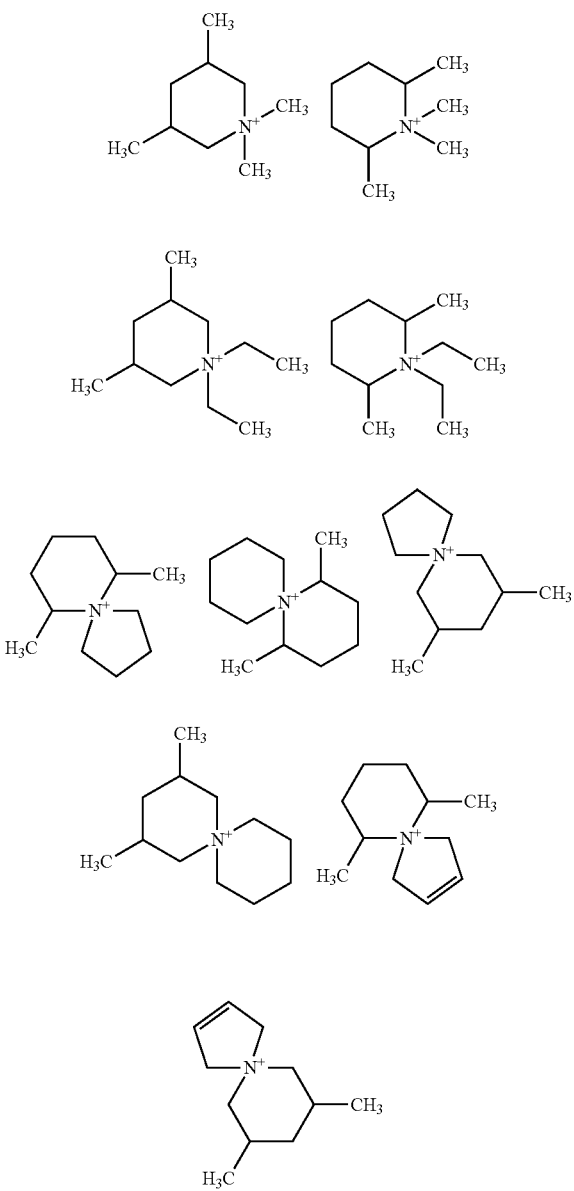

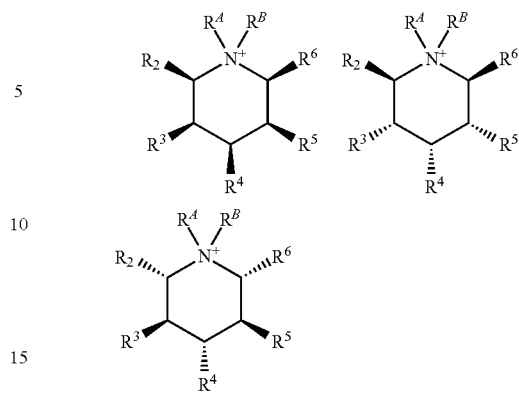

Each of these stereoisomers can adopt different configurations. In some cases, the use of OSDAs having different stereochemistries, adopting different configurations have been known to result in microporous crystalline molecular sieves having different topologies. For example, in Tsuiji, et al., *Microporous and Mesoporous Materials*, 28 (1999) 519-530, the use of two stereoisomers of an OSDA having the same chemical formula each resulted in a different crystalline topology (BEA and MTW). Moreover, in view of the fact that even slight structural differences of OSDAs can lead to different topologies, or that the same OSDA often results in different topologies under even slight differences in reaction conditions, the discovery that the use of mixtures of isomeric OSDAs results in a common framework is all the more surprising.

In specific embodiments of the present invention, the at least two isomers of the quaternary piperidinium cation of Formula (I) comprise a mixture of cis-N,N-dialkyl-3,5-lupetidinium cation and trans-N,N-dialkyl-3,5-lupetidinium cation, a mixture of cis-N,N-dialkyl-2,6-lupetidinium cation and trans-N,N-dialkyl-3,5-lupetidinium cation, or a combination thereof

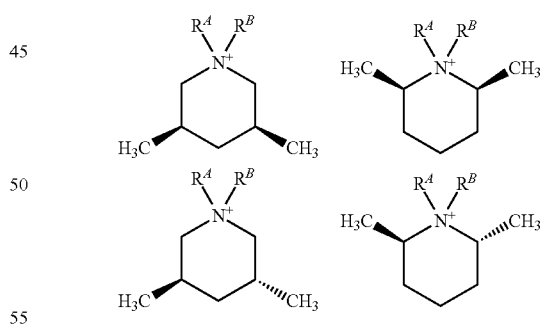

Other embodiments include combinations of the stereoisomers of any of these compounds. While the immediately preceding structures have been characterized without regard to stereochemistry, each of the structures includes stereochemical isomers. For example,

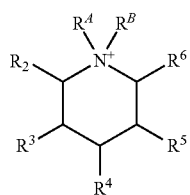

includes individual stereoisomers defined by the relative position of $R^2$, $R^3$, $R^4$, $R^5$, and $R^6$ on the ring, relative to one another. The following shows but three such options:

Again, in this context, the reference to N,N-dialkyl may also include the 5-azonia-spiro[4,5]decane, 5-azonia-spiro[4,5]dec-2-ene, or 6-azonia-spiro[4,5]undecane derivatives described above.

In other embodiments, the at least two isomers of the quaternary piperidinium cation of Formula (I) comprise a mixture of cis-N,N-dimethyl-3,5-lupetidinium cation and trans-N,N-dimethyl-3,5-lupetidinium cation, a mixture of cis-N,N-dimethyl-2,6-lupetidinium cation and trans-N,N-dimethyl-3,5-lupetidinium cation, or a combination thereof

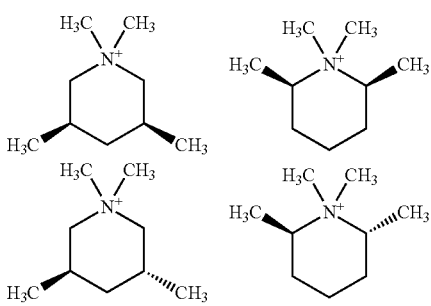

In these embodiments, the ratios of cis and trans in these di-substituted materials may range from about 95% cis/5% trans to about 0% cis/100% trans, though, as described in the Examples, higher levels of trans appears to be preferred. In specific embodiments, the at least two isomers of the quaternary piperidinium cation of Formula (I) comprise a mixture of cis-N,N-dimethyl-3,5-lupetidinium cation and trans-N,N-dimethyl-3,5-lupetidinium cation in a mole ratio of about 98% cis/2% trans to about 0% cis/100% trans. Other embodiments provide that these ratios range from about 98:2 to 95:5, from about 95:5 to 90:10, from 90:10 to 80:20, from 80:20 to 70:30, from 70:30 to 60:40, from 60:40 to 50:50, 50:50 to 40:60, from 40:60 to 30:70, from 30:70 to 20:80, from 20:80 to 10:90, from 10:90 to 0:100, from 95:5 to 75:25, from 75:25 to 50:50, from 50:50 to 25:75, from 25:75 to 5:100, or any combination of two or more of these ranges, including overlapping ranges, for example from 90:10 to 75:25. In each case, the ratios are mole % cis/mol % trans.

As shown in the Examples, higher proportions of trans materials appear to be preferred, at least for the materials tested. For example, as described in the Examples, while pure SSZ-39 can be made with either of the cis-3,5 trans-3,5 or cis-2,6 isomers and mixtures thereof; ii) a relative rate-of-SSZ-39-formation exists as follows: trans-3,5>cis-3,5>cis-2,6. Further, when presented in competition, a preferential incorporation of the trans-3,5 over the cis-3,5 isomer and of the cis-2,6 over the cis-3,5 isomer exists. This observation provides for two interesting conclusions: (1) depending on the economics of the reaction and reactants, it may be useful to use only trans-3,5 piperidinium OSDAs (i.e., as the sole OSDA, without other isomers) or (2) using OSDAs merely enriched in such trans-3,5 piperidinium OSDAs. In this regard, materials prepared by the hydrogenation of pyridine precursors using Raney nickel over those prepared using Pt/H$_2$, owing to the higher proportion of trans-content in the former.

Once prepared, the processes includes embodiments further comprising isolating the crystalline microporous solid. These crystalline solids may be removed from the reaction mixtures by any suitable means (e.g., filtration, centrifugation, etc.) and dried. Such drying may be done in air at temperatures ranging from 25° C. to about 200° C. Typically, such drying is done at a temperature of about 100° C.

These crystalline microporous solid may be further modified, for example, by incorporating metals with the pore structures, either before or after drying, for example by replacing some of the cations in the structures with additional metal cations using techniques known to be suitable for this purpose (e.g., ion exchange). Such cations can include those of rare earth, Group 1, Group 2 and Group 8 metals, for example Ca, Cd, Co, Cu, Fe, Mg, Mn, Ni, Pt, Pd, Re, Sn, Ti, V, W, Zn and their mixtures.

The isolated and optionally post-treated materials may further be treated with oxidizers, such as ozone, to remove the occluded OSDAs and/or calcined in air or inert gas at a temperature in a range of from about 350° C. to about 850° C. In some embodiments, this calcining step may be carried out by holding the crystalline microporous solid at at least one temperature, in some cases two or more temperatures, in a range of from 350° C. to 400° C., from 400° C. to 450° C., from 450° C. to 500° C., from 500° C. to 550° C., from 550° C. to 600° C., from 600° C. to 650° C., from 650° C. to 700° C., from 700° C. to 750° C., from 750° C. to 800° C., from 800° C. to 850° C., or any combination of two or more of these ranges. Depending on the nature of the calcining atmosphere, the materials may be heated to these temperatures for periods of time ranging from 1 to 48 hours or more, to produce a catalytically active product.

Once calcined, the crystalline microporous material may be treated with an aqueous ammonium salt or may be treated under conditions so as to incorporate at least one type of alkaline earth metal or alkaline earth metal oxide, transition metal or transition metal oxide. Individual embodiments include those where the alkaline earth metal or alkaline earth metal oxide or transition metal or transition metal oxide. This may be accomplished, for example by chemical vapor deposition or chemical precipitation. As used herein, the term "transition metal" refers to any element in the d-block of the periodic table, which includes groups 3 to 12 on the periodic table. In actual practice, the f-block lanthanide and actinide series are also considered transition metals and are called "inner transition metals. Scandium, yttrium, titanium, zirconium, vanadium, manganese, chromium, molybdenum, tungsten, iron, ruthenium, osmium, cobalt, rhodium, iridium, nickel, palladium, platinum, copper, silver, gold, or mixtures thereof are preferred.

Intermediate Reaction Compositions

As described elsewhere, the compositions used to prepare these crystalline microporous materials are also considered within the scope of the present disclosure. All of the descriptions used to describe the inventive processes are also considered to apply to these compositions. In an abundance of caution, some of these are presented here, but these descriptions should not be considered to exclude embodiments provided elsewhere.

Included in these embodiments are compositions comprising
(a) at least one source of silicon oxide, germanium oxide, or a combination thereof;
(b) water;
(c) an organic structure directing agent mixture comprising at least two isomers of the quaternary piperidinium cation of Formula (I):

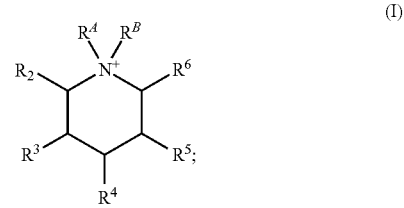

and
(d) a compositionally consistent crystalline microporous solid of an AEI framework;

wherein:

R$^A$ and R$^B$ are independently a C$_{1-3}$ alkyl, or together with the N to which they are bound form a 5 or 6 membered saturated or unsaturated ring; and R$^2$, R$^3$, R$^4$, R$^5$, and R$^6$ are independently H or C$_{1-3}$ alkyl, provided at least one, preferably two of R$^2$, R$^3$, R$^4$, R$^5$, and R$^6$ are independently C$_{1-3}$ alkyl.

In some embodiments, the composition, further comprising at least one source of aluminum oxide, boron oxide, gallium oxide, hafnium oxide, iron oxide, tin oxide, titanium oxide, indium oxide, vanadium oxide, zirconium oxide, or a combination thereof.

These sources of silicon oxide, germanium oxide, aluminum oxide, boron oxide, gallium oxide, hafnium oxide, iron oxide, tin oxide, titanium oxide, indium oxide, vanadium oxide, zirconium oxide, and any combination thereof are among those described elsewhere with respect to the processes. Similarly, any of the options described in the process for the structures of the OSDAs (both cationic organic structure and the anions) are considered embodiments here.

As used herein, the term "compositionally consistent" here refers to a composition having a stoichiometry resulting from the crystallization of the of oxide precursors in the presence of the quaternary piperidinium cation. In some of these embodiments, for example, this feature is intended to reflect a composition which is the result of at least a partial progression of the processes described elsewhere.

While the processes and the corresponding reaction mixtures have been shown to result in topologically pure materials (in the case of the Examples, SSZ-39), it is not necessary that this be the case. For example, some embodiments may result in crystalline mixtures of two or more topologies. These are also considered within the scope of the present invention.

In still other embodiments, the crystalline microporous solid of these compositions may contains a portion of the one or both—typically both—of the at least two isomers of the quaternary piperidinium cation of Formula (I) within their pore structures. These may be identified using, for example $^{13}$C NMR or any of the methods defined in the Examples. The relative proportions of the two or more isomers need not be the same in the pores as in the bulk of the composition, and typically the two proportions are not the same. It is a particular feature of the present invention that the piperidinium OSDAs retain their original structures, including their stereochemical conformations during the synthetic processes, these structures being compromised during the subsequent calcinations.

In some embodiments, depending on the ratio and amounts of the ingredients of the compositions, these compositions take the form of a gel.

Crystalline Microporous Compositions

In addition to the processing and process compositions, the microcrystalline products are also considered within the scope of the present invention. In particular, any product prepared by these inventive methods is considered an embodiment of this invention. Again, in preferred embodiments, the crystalline microporous solid is preferably one of entirely AEI topology. But separate embodiments also provide that the crystalline microporous solid may also contain other structural phases or phase mixtures, for example of other 8-MR zeolites.

These embodiments describing the crystalline microporous solid of AEI topology may be distinguished by those prepared from the hydrothermal treatments and those after calcination. In some embodiments, the products resulting from the hydrothermal treatments can be characterized by the presence of the at least two isomers of the quaternary piperidinium cation of Formula (I) occluded within their pores:

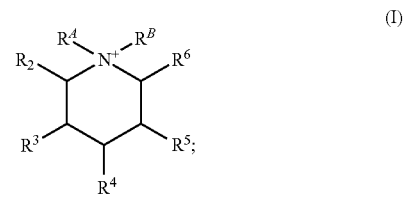

(I)

wherein:

R$^A$ and R$^B$ are independently a C$_{1-3}$ alkyl, or together with the N to which they are bound form a 5 or 6 membered saturated or unsaturated ring; and R$^2$, R$^3$, R$^4$, R$^5$, and R$^6$ are independently H or C$_{1-3}$ alkyl, provided at least two of R$^2$, R$^3$, R$^4$, R$^5$, and R$^6$ are independently C$_{1-3}$ alkyl.

Again, these occluded structures may include any and all of the permutations described for the piperidinium cations as separate embodiments of these structures.

Use of the Inventive Compositions

The calcined crystalline microporous solids, calcined or doped or treated with the catalysts described herein may also be used as catalysts for a variety of chemical reactions, including hydrocracking hydrocarbons, dewaxing hydrocarbon feedstocks, isomerizing hydrocarbons including olefins, producing higher molecular weight hydrocarbons from lower molecular weight hydrocarbons, converting lower alcohols and other oxygenated hydrocarbons to produce liquid products including olefins, reducing the content of oxides of nitrogen, and separating nitrogen from a nitrogen-containing gas mixture. In each case, the processes include contacting the respective feedstock with the catalyst under conditions sufficient to affect the transformation. Such transformations are known to those of ordinary skill in the art.

In various embodiments, the crystalline microporous solids mediate or catalyze an array of chemical transformation. These include processes comprising carbonylating DME with CO at low temperatures, reducing NOx with methane, reducing NO$_X$ with an ammonia source, cracking, dehydrogenating, converting paraffins to aromatics, MTO, isomerizing xylenes, disproportionating toluene, alkylating aromatic hydrocarbons, oligomerizing alkenes, aminating lower alcohols, separating and sorbing lower alkanes, hydrocracking a hydrocarbon, dewaxing a hydrocarbon feedstock, isomerizing an olefin, producing a higher molecular weight hydrocarbon from lower molecular weight hydrocarbon, reforming a hydrocarbon, converting a lower alcohol or other oxygenated hydrocarbon to produce an olefin products, reducing the content of an oxide of nitrogen contained in a gas stream, or separating nitrogen from a nitrogen-containing gas mixture by contacting the respective feedstock with the crystalline microporous solid of the present invention under conditions sufficient to affect the named transformation.

In particular, embodiments comprising contacting methanol with the crystalline microporous solid of the present invention under conditions sufficient to convert the methanol to at least one type of olefin are considered within the scope of the present invention.

More specifically, and as follows, the crystalline solid materials of the present invention will be useful in at least some of the following applications, but are especially useful in converting lower alcohols and other oxygenated hydrocarbons to olefins, reducing the content of nitrogen oxides, and separating nitrogen from a nitrogen-containing gas mixture.

This invention also provides processes for converting lower alcohols and other oxygenated hydrocarbons, each process comprising contacting said lower alcohol (for example, methanol, ethanol, or propanol) or other oxygenated hydrocarbon with a catalyst comprising a crystalline microporous solid of this invention under conditions to produce liquid products.

The present invention provides processes for reducing oxides of nitrogen contained in a gas stream wherein each process comprises contacting the gas stream with a crystalline microporous solid of this invention. The crystalline microporous solid may contain a metal or metal ions (such as cobalt, copper, iron, or mixtures thereof) capable of catalyzing the reduction of the oxides of nitrogen, which may be conducted in the presence of excess of oxygen. In preferred embodiments, the gas stream is the exhaust stream of an internal combustion engine.

Some embodiments provide processes for converting hydrocarbons, each process comprising contacting a hydrocarbon feed at appropriate conditions with a catalyst comprising a crystalline microporous solid of this invention. The crystalline material may be predominantly in the hydrogen form, partially acidic or substantially free of acidity, depending on the process. The crystalline microporous may also contain any one or more of the transition metal catalysts described elsewhere herein.

Other independent embodiments provide processes for hydrocracking, dewaxing, and improving the viscosity index of a dewaxed product of a waxy hydrocarbon feed, each process comprising contacting a (waxy) hydrocarbon feedstock under appropriate conditions with a catalyst comprising a crystalline microporous solid of the present invention. In such embodiments, the catalyst is preferably in the hydrogen form.

Additional embodiments include those processes for producing a $C_{20+}$ lubricant oil from a $C_{20+}$ olefin feed, each process comprising isomerizing said olefin feed under appropriate conditions over a catalyst comprising at least one transition metal catalyst and a crystalline microporous solid of this invention. The crystalline microporous solid is preferably predominantly in the hydrogen form. C4 to C7 hydrocarbons, preferably olefins, may also be isomerized by contacting a feed having normal and/or slightly branched C4 to C7 hydrocarbons under suitable conditions with a catalyst comprising a crystalline microporous solid of the present invention. Again, the crystalline microporous solid is preferably predominantly in the hydrogen form and may be impregnated with at least one transition metal, preferably platinum. The catalyst may further be calcined in a steam/air mixture at an elevated temperature after impregnation of the transition metal.

Still further embodiments include those processes for isomerization dewaxing a raffinate. In such embodiments, each process comprises contacting said raffinate in the presence of added hydrogen with a catalyst comprising at least one transition metal and a crystalline microporous solid of this invention.

Yet other embodiments provide processes for increasing the octane of a hydrocarbon feedstock to produce a product having an increased aromatics content. In such cases, each process comprises contacting a hydrocarbon feedstock having normal and slightly branched hydrocarbons having a boiling range above about 40° C. and less than about 200° C., under appropriate conditions with a catalyst comprising a crystalline microporous solid of this invention. Preferably, the crystalline microporous solid is substantially free of acidity, having been neutralized with a basic metal. In such processes, the crystalline microporous solid may also contain a transition metal component.

Also provided are catalytic cracking processes, each process comprising contacting a hydrocarbon feedstock in a reaction zone under appropriate conditions in the absence of added hydrogen with a catalyst comprising a crystalline microporous solid as described herein, the microporous solid being preferably predominantly in the hydrogen form. In such catalytic cracking processes, the catalyst may additionally comprise a large pore crystalline cracking component.

Aromatic hydrocarbons may also be alkylated using catalysts of the present invention by contacting at least a molar excess of an aromatic hydrocarbon with a C2 to C20 olefin under suitable conditions and in the presence of a catalyst comprising a crystalline microporous solid of this invention, preferably predominantly in the hydrogen form. In certain embodiments, the olefin is a C2 to C4 olefin, and the aromatic hydrocarbon and olefin are present in a molar ratio of about 4:1 to about 20:1, respectively. The aromatic hydrocarbon may include benzene, toluene, ethylbenzene, xylene, or a mixture thereof.

Aromatic hydrocarbons may also be transalkylated by contacting an aromatic hydrocarbon with a polyalkyl aromatic hydrocarbon under suitable conditions in the presence of a catalyst comprising a crystalline microporous solid of this invention, again preferably predominantly in the hydrogen form. The aromatic hydrocarbon and the polyalkyl aromatic hydrocarbon are typically present in a molar ratio of from about 1:1 to about 25:1, respectively. The aromatic hydrocarbon may include benzene, toluene, ethylbenzene, xylene, or mixtures thereof, and the polyalkyl aromatic hydrocarbon may be a dialkylbenzene.

The processes to convert paraffins to aromatics, each of which process comprises contacting paraffins under conditions which cause paraffins to convert to aromatics with a catalyst comprising a crystalline microporous solid of this invention, said catalyst comprising gallium, zinc, or a compound of gallium or zinc.

In accordance with this invention there is also provided processes for isomerizing olefins, each process comprising contacting said olefin under conditions which cause isomerization of the olefin with a catalyst comprising a crystalline microporous solid of this invention.

Further provided in accordance with this invention are processes for isomerizing an isomerization feed, each process comprising an aromatic C8 stream of xylene isomers or mixtures of xylene isomers and ethylbenzene, wherein a more nearly equilibrium ratio of ortho-, meta- and para-xylenes is obtained, said process comprising contacting said feed under isomerization conditions with a catalyst comprising the zeolite of this invention.

The present invention further provides processes for oligomerizing olefins, each process comprising contacting an olefin feed under oligomerization conditions with a catalyst comprising a crystalline microporous solid of this invention.

Specific conditions for each of these transformations are known to those of ordinary skill in the art. Exemplary conditions for such reactions/transformations may also be found in WO/1999/008961, which is incorporated by reference herein in its entirety for all purposes.

Depending upon the type of reaction which is catalyzed, the microporous solid may be predominantly in the hydrogen form, partially acidic or substantially free of acidity. As used herein, "predominantly in the hydrogen form" means that, after calcination, at least 80% of the cation sites are occupied by hydrogen ions and/or rare earth ions.

The following listing of embodiments is intended to complement, rather than displace or supersede, the previous descriptions.

Embodiment 1. A process comprising hydrothermally treating a composition comprising:
(d) at least one source of silicon oxide, germanium oxide, or a combination thereof;
(e) water; and
(f) an organic structure directing agent mixture comprising at least two isomers of the quaternary piperidinium cation of Formula (I):

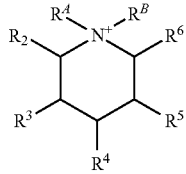

(I)

under conditions effective to crystallize a crystalline composition having an AEI framework topology;
wherein
$R^A$ and $R^B$ are independently a $C_{1-3}$ alkyl, or together with the N to which they are bound form a 5 or 6 membered saturated or unsaturated ring; and
$R^2$, $R^3$, $R^4$, $R^5$, and $R^6$ are independently H or $C_{1-3}$ alkyl, provided at least one (i.e., one, two, three, four, or five) of $R^2$, $R^3$, $R^4$, $R^5$, and $R^6$ are independently $C_{1-3}$ alkyl.

The use of sources of silicon oxide, germanium oxide, and any combination thereof represent individual and independent sub-Embodiments. The presence of sources of silicon oxide, either by themselves or in combination with sources of germanium is preferred.

In certain of these sub-Embodiments, at least two of $R^2$, $R^3$, $R^4$, $R^5$, and $R^6$ are independently $C_{1-3}$ alkyl. The sub-Embodiments in which one, two, three, four, or five of $R^2$, $R^3$, $R^4$, $R^5$, and $R^6$ are independently $C_{1-3}$ alkyl are each considered independent Embodiments. Moreover, reference to "isomers" in the term "at least two isomers of the quaternary piperidinium cation of Formula (I)" refers to both structural and stereochemical isomers.

Embodiment 2. The process of Embodiment 1, wherein the composition further comprises at least one source of aluminum oxide, boron oxide, gallium oxide, hafnium oxide, iron oxide, tin oxide, titanium oxide, indium oxide, vanadium oxide, zirconium oxide, or a combination thereof.

Within this context, the use of sources of aluminum oxide, boron oxide, gallium oxide, hafnium oxide, iron oxide, tin oxide, titanium oxide, indium oxide, vanadium oxide, zirconium oxide, and any combination thereof represent individual and independent sub-Embodiments. The presence of sources of aluminum oxide, either by themselves or in combination with sources of any of these other oxides is preferred.

Embodiment 3. The process of Embodiment 1 or 2, wherein $R^2=R^4=R^6=H$.

Embodiment 4. The process of any one of Embodiments 1 to 3, wherein $R^3=R^5=$methyl.

Embodiment 5. The process of Embodiment 1 or 2, wherein $R^3=R^4=R^5=H$.

Embodiment 6. The process of any one of Embodiments 1, 4, or 5, wherein $R^2=R^6=$methyl.

Embodiment 7. The process of any one of Embodiments 1 to 6, wherein $R^A$ and $R^B$ are independently a $C_{1-3}$ alkyl, preferably methyl or ethyl, more preferably methyl.

Embodiment 8. The process of any one of claims 1 to 6, wherein both $R^A$ and $R^B$, together with the N to which they are bound, form a spiro-pyrrolidinium or spiro-piperidinium moiety:

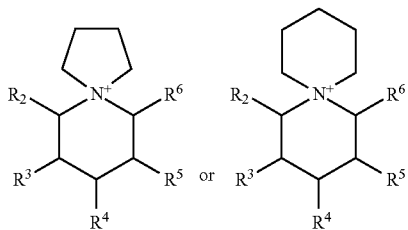

Embodiment 9. The process of any one of claims 1 to 6, wherein both $R^A$ and $R^B$, together with the N to which they are bound, form a spiro-2,5-dihydro-1H-pyrrolium moiety:

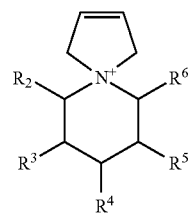

Embodiment 10. The process of any one of Embodiments 1 to 9, wherein at least two isomers of the quaternary piperidinium cation of Formula (I) are structural isomers of one another.

Embodiment 11. The process of any one of Embodiments 1 to 10, wherein at least two isomers of the quaternary piperidinium cation of Formula (I) are stereo-isomers of one another.

Embodiment 12. The process of any one of Embodiments 1 to 11, wherein the quaternary piperidinium cation of Formula (I) is an N,N-dialkyl-3,5-lupetidinium cation, N,N-dialkyl-2,6-lupetidinium cation, or a combination thereof. Again, in this regard, the reference to N,N-dialkyl may also include a spiro-C4-6 alkylene or alkenylene piperidinium cation (as described structurally in Embodiments 8 and 9).

Embodiment 13. The process of Embodiment 11, wherein the quaternary piperidinium cation of Formula (I) is an N,N-dimethyl-3,5-lupetidinium cation, N,N-dimethyl-2,6-lupetidinium cation, N,N-diethyl-3,5-lupetidinium cation, N,N-diethyl-2,6-lupetidinium cation, a 6,10-dimethyl-5-azonia-spiro[4.5]decane, a 1,5-dimethyl-6-azonia-spiro[5.5]undecane, a 7,9-dimethyl-5-azonia-spiro[4.5]decane, a 2,4-dimethyl-6-azonia-spiro[5.5]undecane, or a combination thereof.

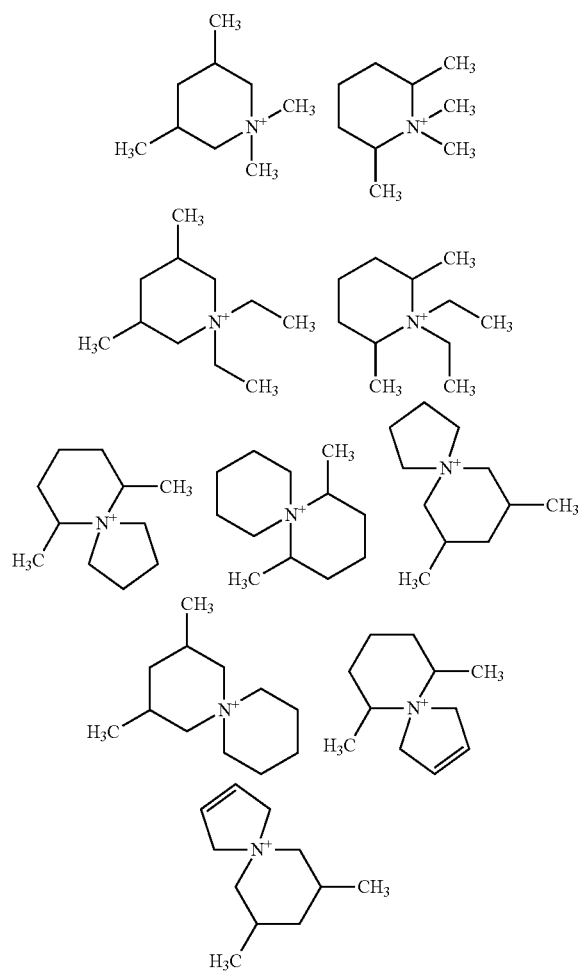

Embodiment 14. The process of any one of Embodiments 1 to 7, wherein the at least two isomers of the quaternary piperidinium cation of Formula (I) comprise a mixture of cis-N,N-dialkyl-3,5-lupetidinium cation and trans-N,N-dialkyl-3,5-lupetidinium cation, a mixture of cis-N,N-dialkyl-2,6-lupetidinium cation and trans-N,N-dialkyl-3,5-lupetidinium cation, or a combination thereof

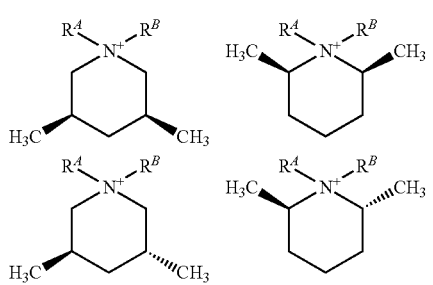

Embodiment 15. The process of Embodiment 14, wherein the at least two isomers of the quaternary piperidinium cation of Formula (I) comprise a mixture of cis-N,N-dimethyl-3,5-lupetidinium cation and trans-N,N-dimethyl-3,5-lupetidinium cation, a mixture of cis-N,N-dimethyl-2,6-lupetidinium cation and trans-N,N-dimethyl-3,5-lupetidinium cation, or a combination thereof.

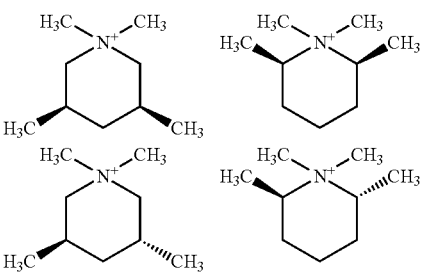

Embodiment 16. The process of Embodiment 1 or 2, wherein the at least two isomers of the quaternary piperidinium cation of Formula (I) comprise a mixture of cis-N,N-dimethyl-3,5-lupetidinium cation and trans-N,N-dimethyl-3,5-lupetidinium cation in a ratio of about 98% cis/2% trans to about 0% cis/100% trans. Independent sub-Embodiments of this include those where the ratio is from about 98:2 to 95:5, from about 95:5 to 90:10, from 90:10 to 80:20, from 80:20 to 70:30, from 70:30 to 60:40, from 60:40 to 50:50, 50:50 to 40:60, from 40:60 to 30:70, from 30:70 to 20:80, from 20:80 to 10:90, from 10:90 to 0:100, from 100:0 to 75:25, from 75:25 to 50:50, from 50:50 to 25:75, from 25:75 to 0:100, or any combination of two or more of these ranges, including overlapping ranges, for example from 90:10 to 75:25.

Embodiment 17. The process of any one of Embodiments 1 to 16, wherein the organic structure directing agent mixture comprises a bromide, chloride, fluoride, iodide, or hydroxide salt, preferably a hydroxide of the at least two isomers of the quaternary piperidinium cation of Formula (I). Other anions may also be considered, including acetates, nitrates, or sulfates.

Embodiment 18. The process of any one of Embodiments 1 to 17, wherein the source of silicon oxide comprises a silicate, silica hydrogel, silicic acid, fumed silica, colloidal silica, tetra-alkyl orthosilicate, a silica hydroxide or combination thereof, preferably sodium silicate or tetraorthosilicate.

Embodiment 19. The process of any one of Embodiments 2 to 18, wherein the source of aluminum oxide comprises an alkoxide, hydroxide, or oxide of aluminum, a sodium aluminate, an aluminum siloxide, an aluminosilicate, or combination thereof, preferably a sodium aluminate.

Embodiment 20. The process of any one of Embodiments 2 to 19, wherein the source of boron oxide, gallium oxide, germanium oxide, hafnium oxide, iron oxide, tin oxide, titanium oxide, indium oxide, vanadium oxide, zirconium oxide, or combination or mixture thereof comprises an alkoxide, hydroxide, oxide, or combination thereof of the corresponding metal.

Embodiment 21. The process of any one of Embodiments 2 to 20, wherein the ratio of Si:Al in the composition is in a range of from about 5:1 to about 10:1, from 10:1 to 20:1, from 20:1 to 30:1, from 30:1 to 40:1, from 40:1 to 50:1, from 50:1 to 60:1, from 60:1 to 70:1, from 70:1 to 80:1, from 80:1 to 90:1, from 90:1 to 100:1, from 100:1 to 150:1, from 150:1 to 200:1, from 200:1 to 250:1, or any combination of two or more of these ranges, for example, from about 5:1 to about 250:1, preferably 10:1 to 100:1, more preferably from 30:1 to 50:1.

Embodiment 22. The process of any one of Embodiments 1 to 21, wherein the ratio of water to Si is in a range of from about 2:1 to about 50:1, including ranges of from 2:1 to 5:1, from 5:1 to 10:1, from 10:1 to 20:1, from 20:1 to 30:1, from 30:1 to 40:1, from 40:1 to 50:1, or any combination of two or more of these ranges.

Embodiment 23. The process of any one of Embodiments 1 to 22, wherein the ratio of piperidinium cation to Si is in a range of from about 0.01:1 to about 1:1, including sub-Embodiment ranges of from 0.01 to 0.02:1, from 0.02:1 to 0.05:1, from 0.05:1 to 0.1:1, from 0.1:1 to 0.15:1, from 0.15:1 to 0.2:1, from 0.2:1 to 0.25:1, from 0.25:1 to 0.3:1, from 0.3:1 to 0.4:1, from 0.4:1 to 0.5:1, or any combination of two or more of these ranges, for example, from 0.01:1 to 1:1, from 0.02:1 to 0.5:1, or from 0.5:1 to 0:25:1.

Embodiment 24. The process of any one of Embodiments 1 to 23, wherein the composition to be hydrotreated further comprises aqueous hydroxide. In some cases, the pH of the water is in a range of from 7 to 7.5, from 7.5 to 8, from 8 to 8.5, from 8.5 to 9, from 9 to 9.5, from 9.5 to 10, from 10 to 11, from 11 to 12, from 12 to 13, from 13 to 14, or any combination of two or more of these ranges.

Embodiment 25. The process of Embodiment 21, wherein the ratio of hydroxide to Si in the composition is in a range of from about 0.5:1 to about 1:1, preferably 0.6:1 to 0.8:1. This is inclusive of any hydroxide anion associated with the compound of Formula (I).

Embodiment 26. The process of any one of Embodiments 1 to 25, wherein the hydrothermally treating is done at a temperature in a range of from about 100° C. to about 200° C. for a time effective for crystallizing the crystalline microporous solid.

Embodiment 27. The process of any one of Embodiments 1 to 26, further comprising isolating the crystalline microporous solid.

Embodiment 28. The process of Embodiments 1 to 27, further comprising calcining the crystalline microporous solid at a temperature in a range of from about 350° C. to about 850° C. In sub-Embodiments, this calcining step is carried out by holding the crystalline microporous solid at at least one temperature, in some cases two or more temperatures, in a range of from 350° C. to 400° C., from 400° C. to 450° C., from 450° C. to 500° C., from 500° C. to 550° C., from 550° C. to 600° C., from 600° C. to 650° C., from 650° C. to 700° C., from 700° C. to 750° C., from 750° C. to 800° C., from 800° C. to 850° C., or any combination of two or more of these ranges.

Embodiment 29. The process of Embodiment 28, further comprising treating the calcined material with an aqueous ammonium salt.

Embodiment 30. The process of Embodiment 28, further comprising treating at least some pores of the calcined crystalline microporous solid with at least one type of alkaline earth metal or alkaline earth metal oxide, transition metal or transition metal oxide. Individual embodiments include those where the alkaline earth metal or alkaline earth metal oxide or transition metal or transition metal oxide comprises Ca, Cd, Co, Cr, Cu, Fe, Mg, Mn, Mo, Ni, Pd, Pt, Re, Sn, Ti, V, W, or Zn, either individually or in any combination thereof.

Embodiment 31. A composition comprising:
(a) at least one source of silicon oxide, germanium oxide, or a combination thereof;
(b) water;
(c) an organic structure directing agent mixture comprising at least two isomers of the quaternary piperidinium cation of Formula (I):

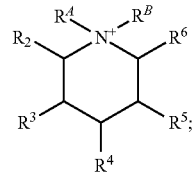

and
(d) a compositionally consistent crystalline microporous solid of an AEI framework;
wherein:
$R^A$ and $R^B$ are independently a $C_{1-3}$ alkyl, or together with the N to which they are bound form a 5 or 6 membered saturated or unsaturated ring; and
$R^2$, $R^3$, $R^4$, $R^5$, and $R^6$ are independently H or $C_{1-3}$ alkyl, provided at least one, preferably two of $R^2$, $R^3$, $R^4$, $R^5$, and $R^6$ are independently $C_{1-3}$ alkyl.

Embodiment 32. The composition of Embodiment 31, further comprising at least one source of aluminum oxide, boron oxide, gallium oxide, hafnium oxide, iron oxide, tin oxide, titanium oxide, indium oxide, vanadium oxide, zirconium oxide, or a combination thereof.

Within the context of this Embodiment, the use of sources of aluminum oxide, boron oxide, gallium oxide, hafnium oxide, iron oxide, tin oxide, titanium oxide, indium oxide, vanadium oxide, zirconium oxide, and any combination thereof represent individual and independent sub-Embodiments. The presence of sources of aluminum oxide, either by themselves or in combination with sources of any of these other oxides is preferred.

Embodiment 33. The composition of Embodiment 31 or 32, wherein the crystalline microporous solid contains a portion of the one or both of the at least two isomers of the quaternary piperidinium cation of Formula (I).

Embodiment 34. The composition of any one of Embodiments 31 to 33, wherein the composition further comprises aqueous hydroxide.

Embodiment 35. The composition of any one of Embodiments 31 to 34 comprising a gel.

Embodiment 36. A crystalline microporous solid comprising one of AEI topology prepared by the process of any one of Embodiments 1 to 27. In preferred embodiments, the crystalline microporous solid is preferably one of entirely AEI topology. But separate Embodiments also provide that the crystalline microporous solid may also contain other structural phases or phase mixtures, for example of other 8-MR zeolites.

Embodiment 37. A crystalline microporous solid of AEI topology prepared by the process of any one of Embodiments 28 to 30.

Embodiment 38. An isolated crystalline microporous solid of AEI topology comprising pores, at least some of which pores are occluded with at least two isomers of the quaternary piperidinium cation of Formula (I)

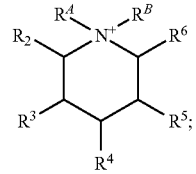

wherein:

$R^A$ and $R^B$ are independently a $C_{1-3}$ alkyl, or together with the N to which they are bound form a 5 or 6 membered saturated or unsaturated ring; and $R^2$, $R^3$, $R^4$, $R^5$, and $R^6$ are independently H or $C_{1-3}$ alkyl, provided at least two of $R^2$, $R^3$, $R^4$, $R^5$, and $R^6$ are independently $C_{1-3}$ alkyl.

Embodiment 39. A process comprising carbonylating DME with CO at low temperatures, reducing NOx with methane, reducing $NO_X$ with an ammonia source, cracking, dehydrogenating, converting paraffins to aromatics, MTO, isomerizing xylenes, disproportionating toluene, alkylating aromatic hydrocarbons, oligomerizing alkenes, aminating lower alcohols, separating and sorbing lower alkanes, hydrocracking a hydrocarbon, dewaxing a hydrocarbon feedstock, isomerizing an olefin, producing a higher molecular weight hydrocarbon from lower molecular weight hydrocarbon, reforming a hydrocarbon, converting a lower alcohol or other oxygenated hydrocarbon to produce an olefin products, reducing the content of an oxide of nitrogen contained in a gas stream, or separating nitrogen from a nitrogen-containing gas mixture by contacting the respective feedstock with the crystalline microporous solid of Embodiment 37 under conditions sufficient to affect the named transformation.

Embodiment 40. A process comprising contacting methanol with the crystalline microporous solid of Embodiment 37 under conditions sufficient to convert the methanol to at least one type of olefin.

EXAMPLES

The following Examples are provided to illustrate some of the concepts described within this disclosure. While each Example is considered to provide specific individual embodiments of composition, methods of preparation and use, none of the Examples should be considered to limit the more general embodiments described herein.

In the following examples, efforts have been made to ensure accuracy with respect to numbers used (e.g. amounts, temperature, etc.) but some experimental error and deviation should be accounted for. Unless indicated otherwise, temperature is in degrees Celsius, pressure is at or near atmospheric.

Example 1

General Methods

Example 1.1

Materials and Methods

The organics were provided by SACHEM Inc. in either chloride or hydroxide form and their synthesis protocols can be found in Example 1.1.1. Hydroxide ion exchanges were performed using Dowex Marathon A (OH—) exchange resin. Titrations were performed using a Mettler-Toledo DL22 autotitrator using 0.01 M HCl as the titrant.

$^{13}$C-CP solid state NMR spectra were recorded on a Bruker 500 MHz spectrometer with a 4 mm rotor at spinning rate of 10 kHz, referenced to adamantane as an external standard. Solid-state $^{27}$Al MAS NMR spectra were acquired on a Bruker AM 300 MHz spectrometer operated at 78.2 MHz using a 90° pulse length of 2 us and a cycle delay time of 1 s. Samples were loaded in a 4 mm $ZrO_2$ rotor and spun at 12 kHz. Chemical shifts were referenced to 1 M aqueous aluminum nitrate solution. Before measurement, samples were hydrated overnight over a saturated KCl solution. Thermogravimetric analysis was performed on a Perkin Elmer STA 6000 with a ramp of 10° C. $min^{-1}$ to 900° C. under air atmosphere. Scanning electron microscopy (SEM) was performed on as-synthesized (washed and dried at 100° C.) samples with a ZEISS 1550 VP FESEM, equipped with an Oxford X-Max SDD X-ray Energy Dispersive Spectrometer (EDS) system for determining the Si/Al ratios of the samples. The calcination of SSZ-39 was performed in dry flowing air by heating to 150° C. at 1° C. $min^{-1}$; holding for 3 h at 150° C., and then heated further to 580° C. at 1° C. $min^{-1}$ and held for 6 h. All powder x-ray diffraction (PXRD) characterization was conducted on a Rigaku MiniFlex II with Cu Kα radiation. Elemental analysis of calcined zeolite samples was performed by Galbraith Labs (Knoxville, Tenn.). All $N_2$ adsorption isotherms were performed at −196° C. with a Quantachrome Autosorb iQ instrument. Prior to analysis, the samples were outgassed under vacuum at 350° C. The t-plot method was used to calculate the micropore volumes on the adsorption branch. For analyzing the organic occluded in the zeolite, the latter was completely dissolved in a 50 wt % HF solution. After neutralization with KOH (exothermic process, cooling required), the solution was dried under a stream of air to remove excess water and then the solids were dried under vacuum at room temperature. Then, $CDCl_3$ was added to dissolve the extracted organic and the isomers were analyzed by $^1$H NMR (quantification) and $^{13}$C NMR.

Example 1.1.1

Preparation of cis-1,2,6-Trimethylpiperidine (fw=127.23)

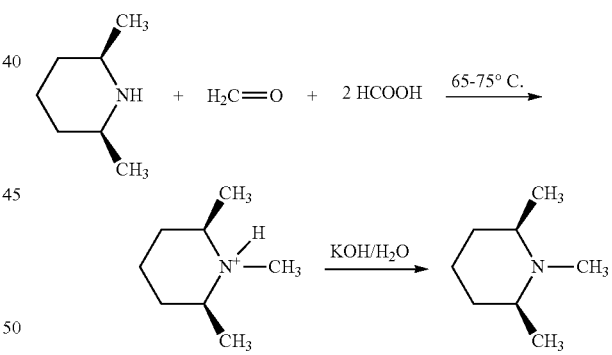

Purified cis-2,6-dimethylpiperidine (2604 g, 23.0 mole, fw=113.20, ~3119 mL, d=0.835) was added in two batches (~1800 mL/~1319 mL) to a container of degassed reagent-grade, 37% aqueous formaldehyde (2516 g, 31.00 mole, fw=30.03, ~2308 mL, formalin with some methanol as stabilizer, d=1.09) over a period of about 3 hours. The reaction was conducted under a slow flow of $N_2$ and the reactor was equipped with a condenser whose cooling coils were maintained at about 1° C. The addition of the cis-2,6-dimethylpiperidine resulted in an exotherm, and the rate of addition was adjusted so that the reaction temperature was maintained in the range 45-50° C.

To this mixture, reagent grade 96% formic acid (2542 g, 53.00 mole, fw=46.03, ~2083 mL, d=1.22) was added in two portions (~1800 mL/~283 mL). The addition of formic acid to the reaction mixture caused a strongly exothermic reaction with vigorous gas evolution (CO$_2$). The addition rate of formic acid was carefully controlled in order to maintain the temperature of the stirring mixture at 65-75° C. Under these conditions, addition time of formic acid was about 3-4 hours. When CO$_2$ evolution was evident, the N2 purging was stopped. The end of the reaction was easily observed after 2.0-2.1 equivalents (~1772 mL) of formic acid is added; the reaction temperature rapidly dropped, and the rate of CO$_2$ evolution rapidly decreased. The entire amount of formic acid was added while the reaction temperature was maintained at about 80° C. using external heating. The reaction mixture was stirred at this temperature for about 6-12 hours in order to ensure complete reaction, and then the reaction mixture was allowed to cool to ambient temperature.

With stirring, KOH pellets or flakes (~1750 g, fw=56.11) were added portion-wise to the stirring mixture until the pH was about 13. After neutralization was complete, the mixture was allowed to stand for two hours at room temperature without stirring to allow for phase separation. The upper product layer was decanted off and divided into two equal portions. The lower layer was discarded. n-Pentane (3.5 L) was added to each portion in a 6 L separatory funnel After standing at room temperature for about 2 hours, additional lower layers formed and were discarded. The other portion of the upper product layer is likewise processed, and the two upper pentane layers are combined. Excess anhydrous MgSO$_4$ was added to this product-containing pentane layer. The mixture was vigorously stirred for about 2 hours. This mixture was filtered through fine-porosity, sintered glass. The clear solution was placed portion-wise in a rotary evaporator to remove the n-pentane solvent. This process was carried out in three stages: (1) a bath temperature at 35° C. at a working pressure of 455 torr; (2) a bath temperature at 40° C. at a working pressure of 380 torr; a bath temperature at 45° C. at a working pressure of 305 torr. The product fractions are combined and allowed to stand at room temperature overnight, Finally, the product, cis-1,2,6-trimethylpiperidine, was filtered through a 0.2 μm nylon filter before use in order to remove magnesium particulates and other solids.

Example 1.1.2

Preparation of cis-1,1,2,6-Tetramethylpiperidinium Chloride (fw=177.72)

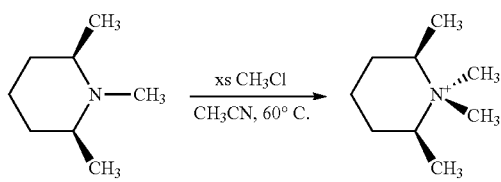

Under a nitrogen purge, a 12 liter round-bottom flask was charged with cis-1,2,6-trimethylpiperidine (2545 g, 20.00 mole, fw=127.23, ~3030 mL, d=0.84), and 4.2 L of reagent-grade acetonitrile. The mechanically stirred mixture was heated to 60° C., and then gaseous methyl chloride (fw=50.49, d=0.92 [liquified gas]), distilled from a pressurized container containing liquified methyl chloride, was carefully bubbled into the stirring reaction mixture. An initial minor reaction exotherm (~2° C.) was observed that subsided within 30-60 minutes. After the exotherm, the reaction temperature was maintained at 60° C. using external heating. The rate of addition of methyl chloride was adjusted so that there was slow refluxing of the methyl chloride from a dry Ice condenser. Almost immediately, white crystals of the product began to crystallize from solution. The progress of the reaction is determined by periodically (every 3 hours) monitoring the reaction mixture using HPLC. The reaction was essentially complete after about 21-30 hours (99+% conversion of the starting amine) An excess of methyl chloride was used to ensure completeness. After the reaction was essentially complete, the reaction flask was briefly purged with N$_2$ to remove part of the excess, unreacted methyl chloride, methyl chloride being very soluble in acetonitrile. The hot reaction mixture was allowed to cool to ambient temperature over a period of about 2-3 hours, and then it is allowed to stand at 4° C. overnight in a refrigerator (4° C.). Under a dry nitrogen atmosphere, the cold mixture was then filtered through medium porosity sintered glass in order to obtain the main part of the product (white crystals, Crop1). The product is hygroscopic in laboratory air. The product is washed with a minimum amount MTBE and then allowed to partially dry by passing dry N$_2$ through the filter cake. The crystals are dried in a vacuum oven overnight (80° C., 20 torr) yielding 3234 g (91%, Crop1). The product did not melt but decomposed at 255-260° C. (dec). MTBE was added to the filtrate and more white microcrystals come out of solution. This material was recovered by filtration (Crop2) and washed (142 g, 4%, Crop2, white crystalline solid). For Crop1, typical purity was 99.6-99.8% (HPLC). For Crop2, typical purity was 98.2-99.2% (HPLC) depending on the purity of the starting amine.

Analyses were carried out using Waters Corp. (Milford, Mass.) gradient HPLC equipped with a Waters 996 PDA detector in tandem with a Dionex/ESA Biosciences (Chelmsford, Mass.) Corona Plus CAD detector and (1) a SIELC Technologies Primesep 200, 5 Nm, 100 Å, 4.6×150 mm SS, mixed-mode surface coating over porous silica, reversed-phase/cation-exchange chromatography column with 4.6×50 guard column (Prospect Heights, Ill.) or (2) a Waters Xbridge BEH 130, 5 Nm, 130 Å, 4.6×250 mm SS column (C18 reversed-phase surface-coating over porous silica) without guard column (Milford, Mass.). Same buffers and gradient method used for both columns.

Sample Injection: 10 μL of a sample solution in 80/20 (v/v) water/acetonitrile w/0.1% HTFA. Flow-Rate: 1.0 mL/min. A buffer: HPLC-grade water+1% (v/v) HPLC-grade acetonitrile+0.1% (v/v) trifluoroacetic acid B buffer: HPLC-grade acetonitrile+1% (v/v) HPLC-grade water+ 0.1% (v/v) trifluoroacetic acid Gradient Method: 100% A 0-1 min 100% A to 100% B 1-61 min 100% B 61-70 min Peak Identification: A=cis-2,6-dimethylpiperidine; B=cis-1,2,6-trimethylpiperidine-conformer 1; C=cis-1,2,6-trimethylpiperidine-conformer 2; D=cis-1,1,2,6-tetramethylpiperidinium chloride I=injection peak Example 1.1.3

Zeolite Syntheses

A general procedure for hydroxide mediated zeolite syntheses was as follows. The organic SDA in its hydroxide form was combined with additional base (1N NaOH, RT Baker) and water in a 23 mL-Teflon Parr reactor. Then a silicon source was added (N° Sodium silicate (PQ Corporation) or Ludox AS-40) as well as an aluminum source (CBV500, a NH$_4$-USY zeolite with Si/Al of 2.6 from Zeolyst). The synthesis gel was then manually stirred with a spatula until a homogenous white gel was obtained. The Teflon Parr reactor was then sealed and placed in a rotating (spinning at 63 rpm) or static oven at temperatures ranging from 125 to 140° C. Alternatively, tetraethylorthosilicate (TEOS) was used as the source of silica. TEOS was combined with the additional base source (1N NaOH) in a 23 mL-Teflon Parr reactor, closed and stirred overnight at room temperature to allow for complete hydrolysis. The lid was then removed and the organic SDA in its hydroxide form as well as the aluminum source (CBV500) were added and stirred till a homogeneous gel was attained. The lid was then removed and ethanol and the appropriate amount of water were allowed to evaporate under a stream of air. It was assumed that all the ethanol evaporated along with the water. Once the appropriate mass was reached the Teflon Parr reactor was sealed and placed in a rotating at 140° C. Sometimes, aliquots of the synthesis gels were taken periodically as follows: quenching the reactor in water, opening the reactor, stirring its contents until homogeneous, and finally removing enough material for PXRD. After washing the aliquots once with water and once with acetone, with intermittent centrifugation, they are left to dry in a 100° C. oven before PXRD measurement. After total synthesis time, the zeolites were collected by centrifugation, washed 3 times with water and once with acetone, with intermittent centrifugation, and then left to dry overnight at 100° C. The yields were calculated as follows: the oven-dry zeolite weight obtained is corrected with the weight loss of organic SDA and water in TGA up to 900° C. (15-18% in a typical synthesis). This corrected weight is assumed to be pure aluminosilicate and is divided by the maximum theoretical oxide ($SiO_2+AlO_2$) formation based on the input silicon and aluminum. The weight of sodium present in the samples is hereby neglected. The weight loss in TGA between 300 and 900° C. was considered to be due to the loss of incorporated OSDA (amine form).

Example 2

Observations on General SSZ-39 Synthesis Considerations

In order to assess the influence of the isomeric forms of the common lupetidines and the possibility of using mixtures of isomeric OSDAs, a standard SSZ-39 recipe was needed. The first synthesis of SSZ-39 in hydroxide mediated syntheses was reported in U.S. Pat. No. 5,958,370. Procedures listed in the patent demonstrate the use of sodium silicate and a zeolite of the FAU topology (USY) as the respective silica and alumina sources. The reported results showed successful syntheses of SSZ-39 with 13 different OSDAs (FIG. 1) from gels with Si/Al ratios around 15. The results also showed that a gel with Si/Al of 50 led to SSZ-39 (with Si/Al ratio of 25). Besides other FAU zeolites, no other sources were presented in this study. Later, Wagner et al., *J. Am. Chem. Soc.* 1999, 122, 263, reported the structure of SSZ-39 and showed that it is the aluminosilicate analogue of SAPO-18 with the AEI framework topology. Wagner reported successful SSZ-39 syntheses from gels with a Si/Al ratio of 15, in analogy to the original patent, whereas attempts to make SSZ-39 in gels with Si/Al ratios of 20 and higher resulted in other phases such as MFI and MTW.

Recently, Moliner et al., *Chem. Commun.* 2012, 48, 8264. reported similar results, confirming the fact that sodium silicate ($Na_2SiO_3$) and FAU precursors in gels with Si/Al ratios 15 and 30 lead to SSZ-39, whereas other sources of inorganics do not lead to SSZ-39. The OSDA used in the latter study was N,N-dimethyl-3,5-lupetidine, but the cis:trans ratio of the organic was not reported. In addition to these hydroxide syntheses, a fluoride-mediated route towards high-silica SSZ-39 has been disclosed using N,N-diethyl-2,6-lupetidine as the SDA. These low-water syntheses are reported to produce SSZ-39 with Si/Al ratios of over 50.

Based on this literature overview, a wide screening of common procedures and sources of inorganics was carried out using cis-N,N-dimethyl-3,5-lupetidine (cis-3,5) as the SDA over a range of Si/Al ratios, and reported in Table I.

TABLE I

Screening approach to an SSZ-39 recipe assess with the N,N-dimethyl-cis-3,5-lupetidine SDA

| Si Source | Al Source | Si/Al | Time, days | Temp, ° C. | Outcome |
|---|---|---|---|---|---|
| LUDOX | $NH_4$-Y (FAU) | 30 | 18 | 140 (160) | MFI/MTW + SSZ-36 |
| LUDOX | $NH_4$-Y | 15 | 12 | 140 (160) | RTH/ITE = SSZ-36 |
| Cabosil | Reheiss | 15 | 12 | 140 | / |
| Sodium silicate | $NH_4$-Y (FAU) | 15 | 12 | 140 | AEI-SSZ-39 (FAU) |
| LUDOX | Na-aluminate | 15 | 12 | 140 | / |
| Cabosil | Reheiss | 15 | 12 | 160 | / |
| Cabosil | Reheiss | 30 | 12 | 160 | / |
| LUDOX | Na-aluminate | 15 | 12 | 160 | / |
| LUDOX | Na-aluminate | 30 | 12 | 160 | /+ MFI |
| Cabosil | LZY-52 | 20 | 6-9 | 160 | /+ FAU |
| Cabosil | $NH_4$-CBV712 | 35 | 6-9 | 175 | MFI/TW |
| Cabosil | Reheiss | 50 | 5-8 | 175 | MFI/MEL |
| TOSOH-390 HUA | | 150 | 6 | 160 | MFI (silicate) |

/ = Amorphous. In-house NH4-FAU has Si/Al = 2.6

Figure 10:
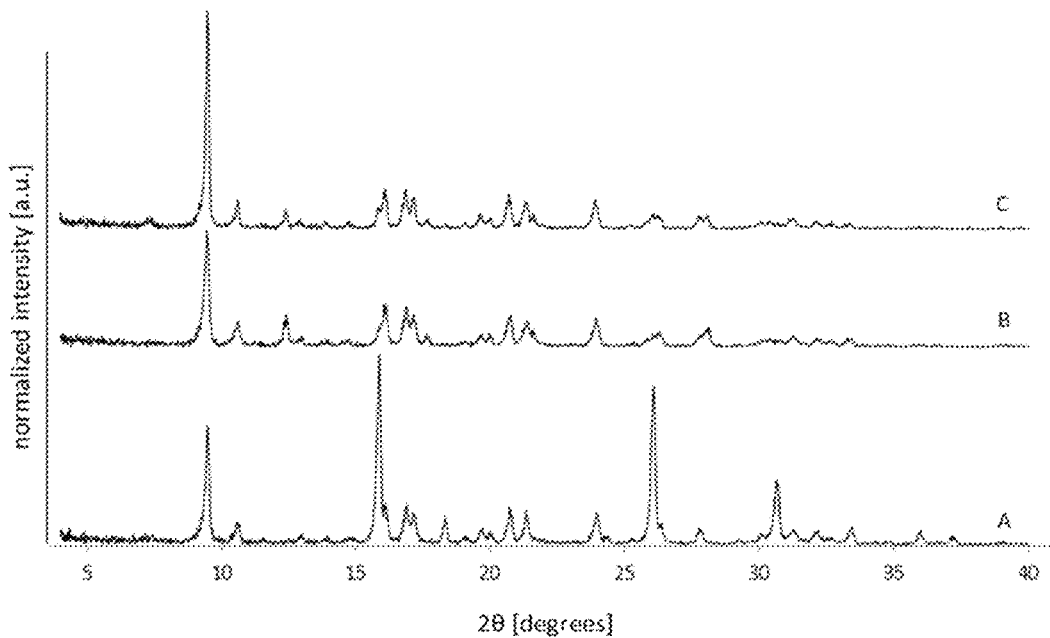
FIG. 10 shows powder XRD patterns of SSZ-39 synthesized with different silica sources and FAU as alumina sources: A) colloidal silica Ludox AS-40, B) tetraethylorthosilicate (TEOS) and C) sodium silicate. Samples prepared using N,N-dimethyl-cis-3,5-lupetidine SDA in rotating oven at 140° C., 6-7 days. Gel composition of A) Si:0.067Al: 0.17SDA:0.710H—:0.54Na:20H$_2$O. B) Si:0.067Al: 0.14SDA:0.650H-:0.51Na:28H$_2$O. C) Si:0.067Al:0.14SDA: 0.650H—:0.51Na:28H$_2$O. The large impurity at 2θ 16 and 26 values in pattern A is indicative of major analcime (ANA topology, dense phase) side-product formation.
Figure 11:
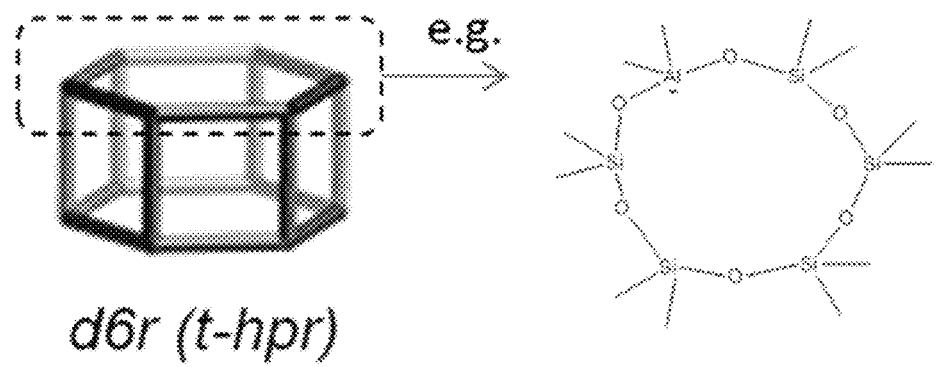
FIG. 11 shows a double six ring composite zeolite building unit (d6r). Each corner of the left structure on the left represents a T-atom. The oxygen atoms are omitted for clarity on the left, but can be seen on the right. Both FAU and AEI can be built up by only translating and linking this composite d6r building block. Other molecular sieves that can be exclusively built with d6r are found within e.g. CHA, KFI, AFX and GME topologies.

In line with literature data, initially only sodium silicate and FAU as inorganic sources yielded SSZ-39. Other recipes, consistent with those reported by Wagner et al., led to SSZ-36 or pentasil type zeolites (e.g., MFI). Sodium silicate is a monomolecular Si source, unlike colloidal Si gels and aerosils. To see whether a monomolecular source of Si is vital, TEOS and colloidal Si were used instead of sodium silicate with the FAU aluminum source. From the results shown in FIG. 10, it was clear that SSZ-39 could be prepared using monomolecular TEOS and colloidal Si as well, but the latter led to the co-formation of a major impurity, analcime (ANA). The FAU Al source on the other hand is more crucial, as no synthesis was found successful without its presence. Remarkably, both AEI and FAU frameworks can be entirely built using only the double six-ring composite building unit (d6r, shown in FIG. 11). Interestingly, a hydrothermal transformation of FAU into AEI zeolites was recently reported, using tetraethylphophonium cations. In general, an optimal gel compositional range was found to be 1Si:0.033-0.066Al:0.07-0.140SDA:0.65-0.71OH—:0.51-0.58Na+:20-30H$_2$O, with OH— being the sum of the NaOH and OSDA(OH—) contents.

Example 3

Observations on Influence of Cis/Trans Isomer Ratio with 3,5-Lupetidine Based OSDAs The hydrogenation of the commercially relevant 3,5-lutidine leads to diastereomeric 3,5-lupetidine mixtures containing both the cis and trans-form depending on the catalysts used. Using metallic Pt and H$_2$ will lead to a product mixture with an 80/20 cis/trans isomer ratio, whereas under certain conditions, Raney Nickel catalysts produce mixtures of 25/75 cis/trans composition. If the amine is methylated before hydrogenation, pure cis-N-methyl-3,5-lupetidine can be synthesized with Pt catalysts. By preparing a nearly pure cis-3,5 isomer, along with an equimolar mixture, the isomeric range between 48/52 and 98/2 (cis-3,5/trans-3,5) could be assessed. This range is in line with the production of these isomers, as it is nearly impossible produce the pure trans-isomer. The influence of diastereo-isomer ratio on the synthesis of SSZ-39 is illustrated by the data shown in Table II where different isomeric mixtures of quaternized N,N-dimethyl-3,5-lupetidinium hydroxide are employed OSDAs in two sets of gels with different Si/Al ratios (15 and 30).

suggested an explanation for the low product yields (20%). Due to the formation of Al-rich SSZ-39, the gel became deficient in Al at some point in the synthesis, and a large fraction of dissolved Si remained unused. For the Si/Al=15 gels, (Table II entries 3 to 5), the conclusions can be drawn as with the samples obtained using Si/Al of 30: the cis/trans ratio of the OSDA had no significant impact on the formation of SSZ-39. The PXRD patterns and TGAs for these syntheses are found in FIG. 12 and FIG. 13, respectively. Additionally, the SSZ-39 morphologies (SEM images in FIG. 14), were similar and closely resemble those reported previously by Moliner. Some clear differences however existed between these syntheses and the ones with Si/Al ratios of 30 in the gel. First, the Si/Al ratios of the products from Si/Al=15 gels were found to be around 6. Although lower than the values obtained from more Al-deficient gels, the product ratios are diverging less from the ratio in the gels (6 to 15 versus 8 to 30) and explain the higher yields from Si/Al=15 gels. Secondly, a closer examination of the PXRDs (FIG. 13) of the Si/Al=15 derived zeolites revealed SSZ-39 as the major phase, but with a trace of the aluminosilicate gismondine (GIS), e.g., the reflection at 2θ=12.4. The origin of this impurity was attributed to the inorganic structure directing nature of the sodium- and hydroxide-rich gel. As seen in Table II entry 6, a gel without organic but with the same total hydroxide content yielded a mixture of mordenite (MOR) and GIS. This (as well as dense phase analcime, ANA) was to be expected in gels with low Si/Al ratios. No such impurities were found in the Si/Al=30 gels (viz. FIG.

TABLE II

Hydroxide Syntheses with Mixtures of cis- and trans-N,N-dimethyl-3,5-lupetidinium Hydroxide Using Sodium Silicate as Silica and NH$_4$-FAU as alumina Sources Gel composition relative to Si [1]

| Entry | Al | cis-3,5 | trans-3,5 | NaOH | cis/trans[2] | time | phase | Si/Al | TGA[3] | Yield |
|---|---|---|---|---|---|---|---|---|---|---|
| 1 | 0.033 | 0.137 | 0.003 | 0.57 | 98/2 | 3 d | SSZ-39 | 7.6 | 19.2% | 19% |
| 2 | 0.033 | 0.067 | 0.073 | 0.57 | 48/52 | 3 d | SSZ-39 | 8.4 | 19.7% | 19% |
| 3 | 0.067 | 0.137 | 0.003 | 0.51 | 98/2 | 6 d | SSZ-39 [4] | 6.2 | 13.4% | 39% |
| 4 | 0.067 | 0.101 | 0.038 | 0.51 | 73/27 | 6 d | SSZ-39 [4] | 6.3 | 13.6% | 39% |
| 5 | 0.067 | 0.067 | 0.073 | 0.51 | 48/52 | 6 d | SSZ-39 [4] | 6.2 | 14.2% | 41% |
| 6 | 0.067 | 0 | 0 | 0.66 | — | 7 d | GIS/MOR | — | — | — |
| 7 | 0.142 | 0.171 | 0.004 | 0.80 | 98/2 | 3 d | GIS | 2.6 | 2.0% | — |

[1] H$_2$O:Si kept at 28 for all entries. NaOH:Si calculated from the total Na content, originating from NaOH addition and sodium silicate. Synthesis in a rotating oven at 140° C.
[2] Ratio of cis-3,5/trans-3,5 isomer.
[3] Weight % loss in TGA between 300° C. and 900° C. relative to the amount of zeolite left at 900° C.
[4] Trace GIS (ANA) impurities noticed in these samples.
[5] GIS recipe in the presence of OSDA with sodium aluminate instead of NH$_4$-FAU and with H$_2$O:Si = 35.

Figure 3:
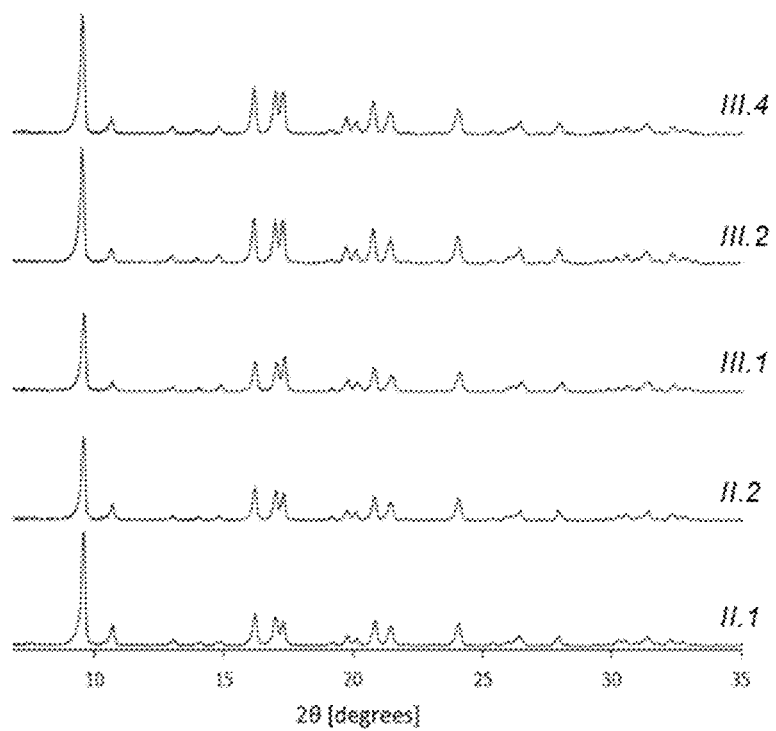
FIG. 3 shows powder XRD patterns for pure as-synthesized SSZ-39 made with different isomeric mixtures in gels with Si/Al 30. Numbers correspond to the entries in Tables II and III: (II.1) 98/2 cis/trans-3,5; (II.2) 48/52 cis/trans-3,5; (III.1) cis-2,6; (III.2) 50/50 cis-3,5/cis-2,6; (III.4) 24/26/50 cis-3,5/trans-3,5/cis-2,6.
Figure 4:
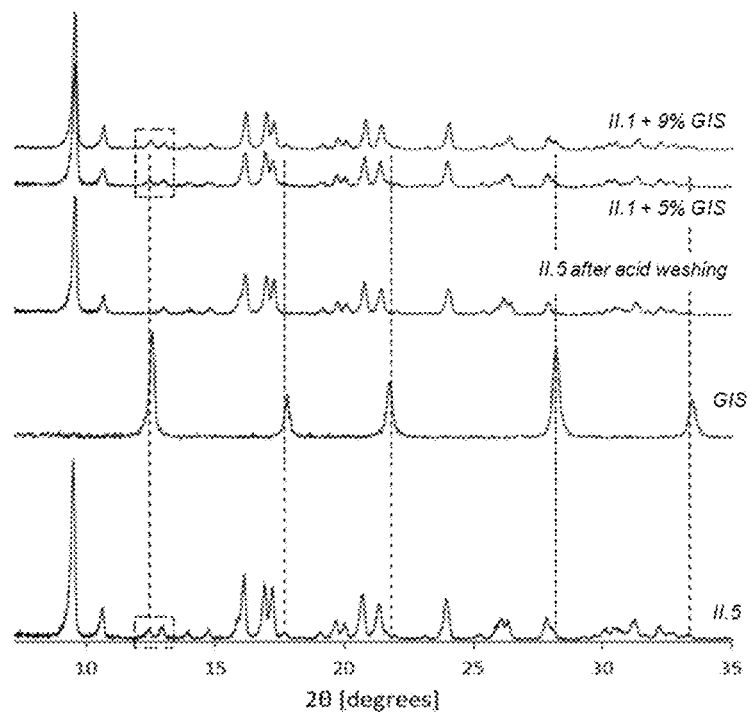
FIG. 4 shows powder XRD patterns of impure SSZ-39 from Table II, entry 5 (II.5, 48/52 cis/trans-3,5), before and after acid washing with 1N HCl for 1 h at 100° C., compared to pure GIS (II.7) and physical mixture of pure SSZ-39 (Table II, entry 1; II.1) and GIS (5 and 9 wt %).
Figure 5:
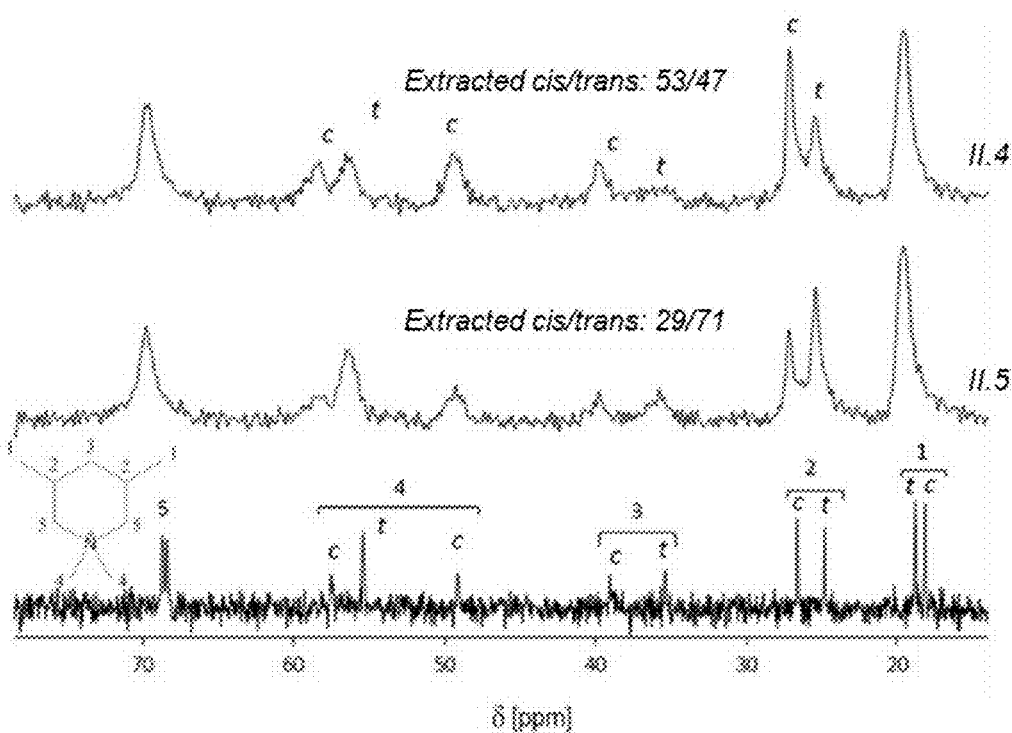
FIG. 5 shows $^{13}$C CP-MAS NMR of the (48/52) cis/trans-3,5 OSDA standard compared to as synthesized SSZ-39 made with different grades of cis-3,5/trans-3,5 according to entries in Table II (Table II, entry 4; II.4) 73/27 and (Table II, entry 5; II.5) 48/52. c=cis, t=trans. The extracted ratios are measured by $^1$H-NMR after SSZ-39 dissolution.
Figure 13:
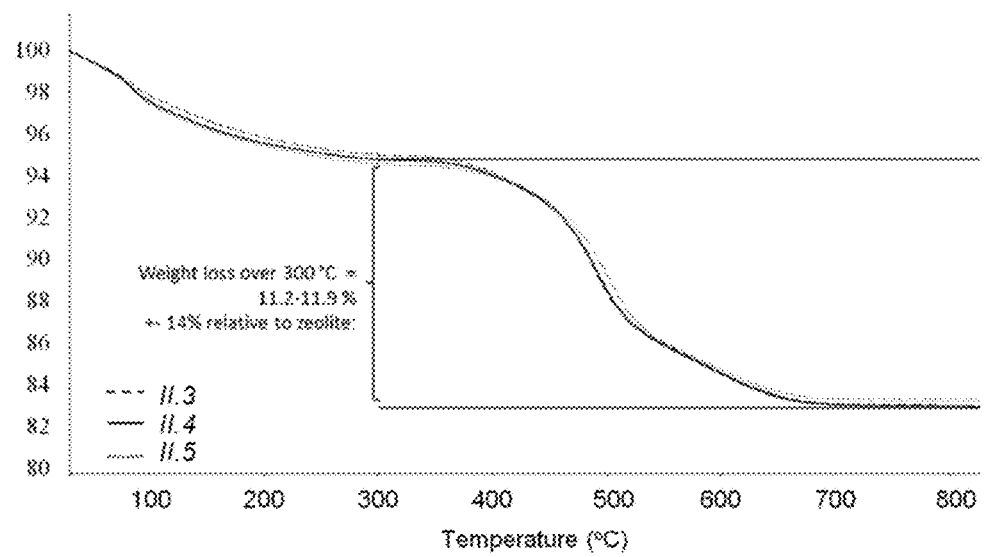
FIG. 13 shows TGA analysess of SSZ-39 made in conditions of Table II, entry 3, 4 and 5. The weight loss of the organic (300° C.-900° C.) with respect to the input 'wet' zeolite was about 11-12%. Normalized on the amount of dry, pure solid recovered at 900° C. (83.5% of the input weight), the amount of included OSDA per zeolite was about 14%.
Figure 15:
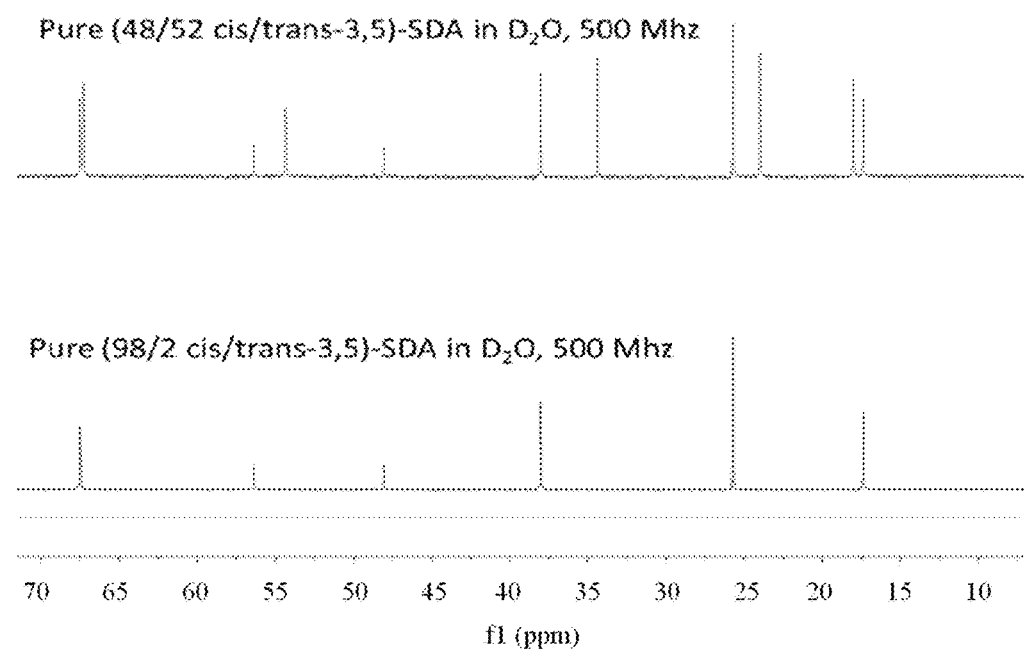
FIG. 15 shows $^{13}$C NMR (liquid phase) analysis of pure cis and 48/52 cis/trans-3,5-lupetidine based SDAs
Figure 14:
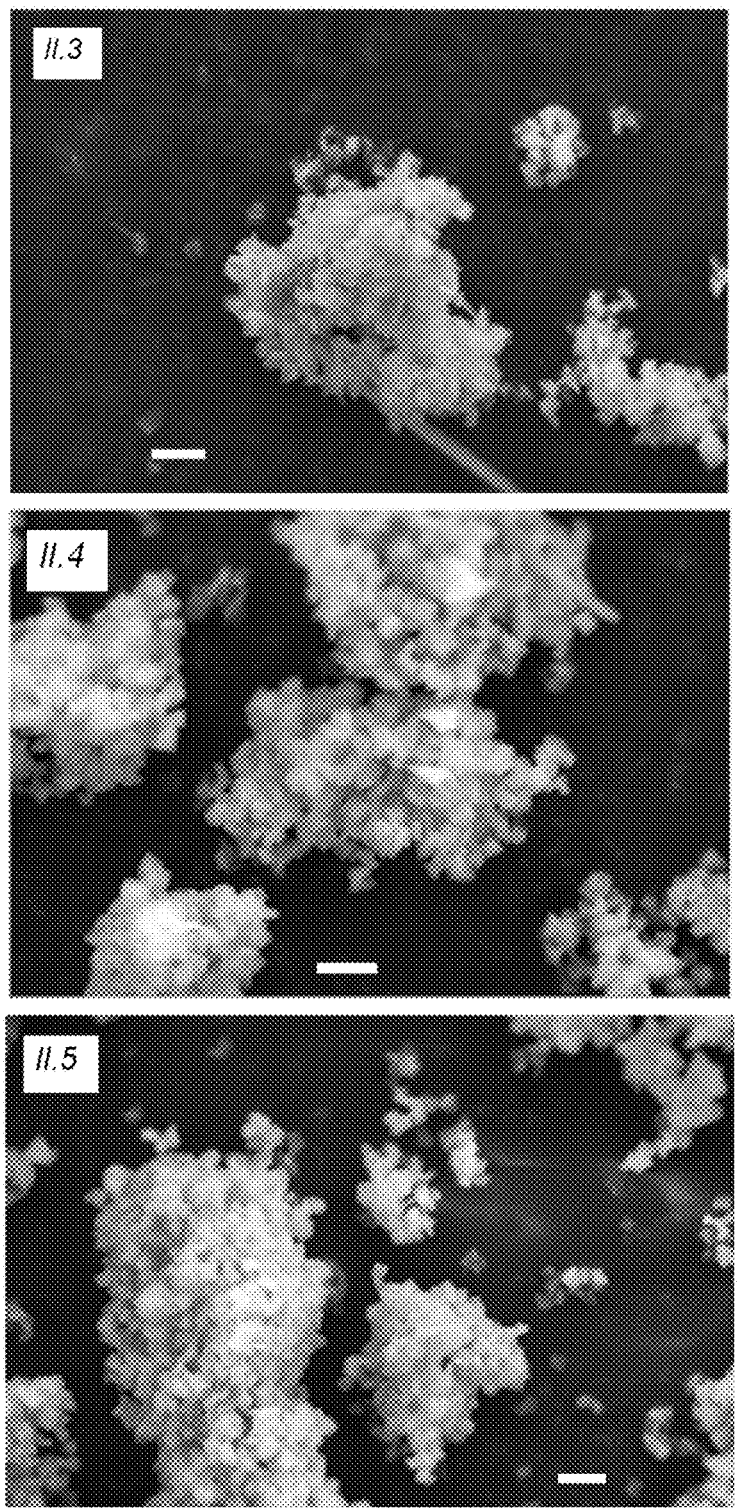
FIG. 14 shows SEM analysis of SSZ-39 made in identical conditions as those in Table II, entries 3, 4 and 5. (repeat experiments, yielding same products, same PXRD.)
Figure 16:
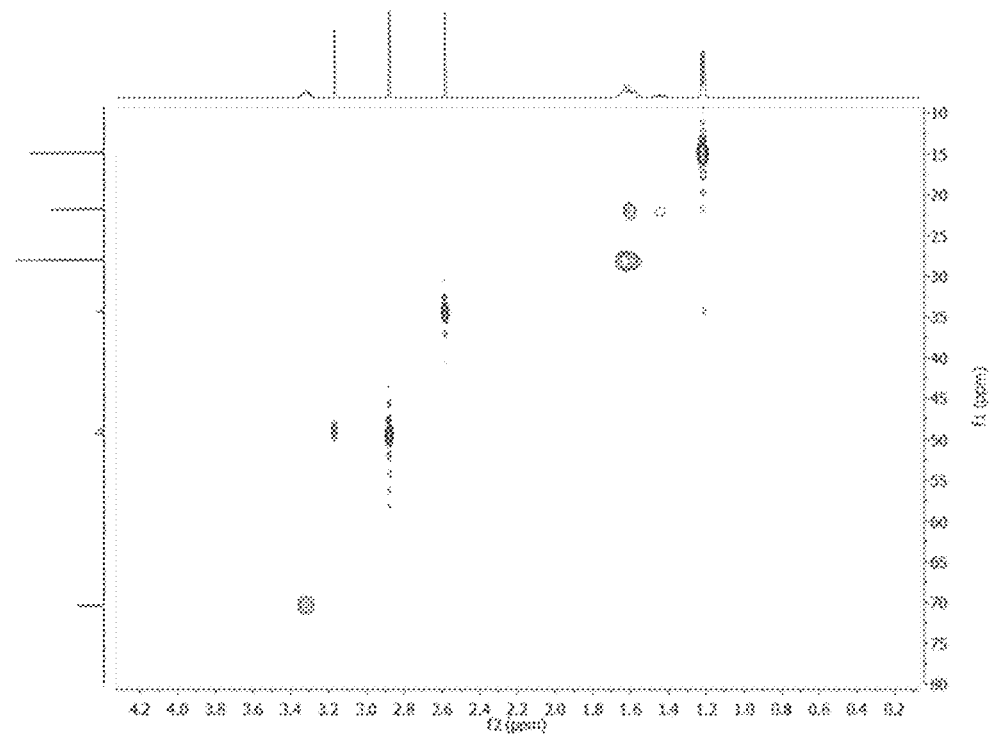
FIG. 16 shows $^1$H-$^{13}$C—HSQC liquid phase NMR analysis of pure cis-2,6-lupetidine based SDA

Entries 1 and 2 in Table II, for Si/Al ratios of 30, revealed no significant influence of the diastereo-isomer ratio of the 3,5-isomer on the preparation of SSZ-39: the produced phase, pure SSZ-39, was identical in each run, as demonstrated by PXRD in FIG. 3 (Trace II.1 and III.2). Additionally, the phase, yield and synthesis time (kinetics) appeared unaffected as well since both syntheses finished in 3 days (based on the absence of reflections of the FAU source in PXRD). Further characterizations of the produced solids were performed by TGA and SEM/EDS analyses. The Si/Al ratios of both SSZ-39 solids were found to be near 8, in line with Moliner et al., *Chem. Commun.* 2012, 48, 8264, and the total amount of incorporated OSDAs were around 20% (ca. filling of 1 organic molecule per cage of the structure or 4 OSDA molecules per unit cell). The product Si/Al values (8) differed distinctly from the ratios in the gels (30). This result 3). Since all three isomer ratios that were used for the solids whose results are shown in FIG. 13, it was concluded that the impurity was not influenced by isomer ratios. For catalytic applications, the presence of trace impurity phases can be a problem. In an effort to remove the impurities, the as-synthesized SSZ-39 (Table II.5) was easily purified by contacting it with a 1 M HCl solution at 100° C. for only 1 h (no stirring, 10 gram of zeolite per liter). This conclusion was evidenced by data shown in FIG. 4 that were from the solids (Table II.5) obtained before and after contacting with HCl. This simple treatment completely dissolved the GIS phase. To further verify this result and to estimate the amount of impurity in the as-made SSZ-39, a pure GIS zeolite was made in presence of the cis-3,5 isomer by using sodium aluminate (entry 7, Table II). The PXRD of this zeolite can be seen in FIG. 2. TGA analysis of the 8MR GIS zeolite confirmed that virtually no organic was incorporated (<2%). The PXRD patterns of physical mixtures of GIS and pure SSZ-39 (the as-made zeolite of Table II.1), shown in FIG. 4, allowed a rough estimate of the level of impurity in Si/Al=15-derived SSZ-39 to be in the order of 5 wt % (based on intensities of the 2θ=12.5 region). Since GIS phases usually have a low Si/Al ratio (i.e., 2.6 in Entry 7), the bulk Si/Al ratio of the treated zeolite rose (from 6.2) to 7.5 as determined by EDS and confirmed by elemental analysis below. The TGA results in Table II demonstrate that the same total amount of organic was incorporated in the SSZ-39 made with different isomer ratios. However, the stereochemistry of the occluded organics in these solids may be different. To address this issue, the occluded organic content was analyzed. Remarkably, $^{13}C$ CP-MAS solid state NMR on as-made samples was able to distinguish the cis from the trans isomer occluded in the cages of SSZ-39 (FIG. 5). While the NMR trace of SSZ-39 made with pure cis-3,5 displayed the 6 characteristic resonances related to the cis-3,5-standard (not shown), the spectra of the SSZ-39 made with the 73/27 (trace II.4) and the 48/52 cis/trans-3,5 mixture (trace II.5) displayed resonances of both cis and trans isomers in SSZ-39. The relative integration of the 27 versus 25 ppm peak hinted to a preferential uptake of the trans isomer with respect to the ratio of the gel (especially visible in the II.5 trace). However, due to the non-quantitative nature of CP-MAS NMR, the isomer ratio inside SSZ-39 was verified by dissolving the as-made materials in HF, extracting the SDAs in CDCl₃ and analyzing them by $^{1}H$-NMR. These isomer ratios are shown above the CP-MAS traces in FIG. 5 and corroborate the preferential incorporation of the trans isomer. The 48/52 gel for instance, produced SSZ-39 with a 29/71 cis/trans ratio. The assignments of the chemical shifts for both isomers were verified using liquid phase NMR and $^{1}H$-$^{13}C$—HSQC (FIGS. 15-16).

Figure 6:
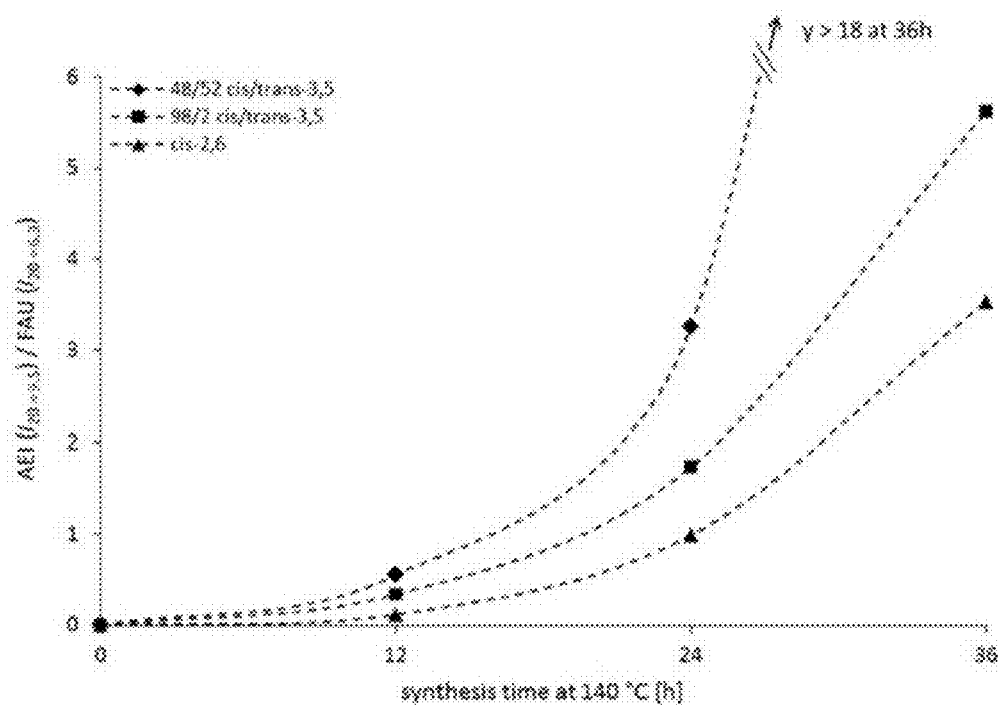
FIG. 6 shows some kinetics of SSZ-39 synthesis with different OSDA isomer ratios. (based on the FAU reagent and AEI product reflections in PXRD). Conditions of Table II, entry 1 and entry 2 and Table III, entry 1.

Although there was a preference for the incorporation of the trans-3,5 isomer, both isomer mixtures as well as nearly-pure cis-3,5 are able to produce SSZ-39. To further investigate this phenomenon, the kinetics at the early stages of SSZ-39 syntheses were studied by taking intermediate samples of syntheses with 98/2 and 48/52 cis/trans-3,5 isomeric ratios after 12, 24 h and 36 h. Because the starting FAU source was still present in these samples, and visible in PXRD, the kinetics of SSZ-39 formation could be assessed by relative comparison of the intensities of the major reflection of AEI (9.5° 2θ) and FAU (6.3° 2θ), as shown in FIG. 6. A clear difference in the kinetics of zeolite formation was noted between the 48/52 mixture and the near pure cis-3,5 isomer, with the high in-trans synthesis notably faster. However, by 3 days of synthesis time, the results from these syntheses were the same (Table II). These initial kinetic data, together with the observed preferential incorporation, point to the fact that the presence of the trans isomer was a positive (or at least faster) for SSZ-39 synthesis.

Example 4

Observations on Influence of 2,6- vs 3,5-Lupetidine Based OSDAs

Figure 12:
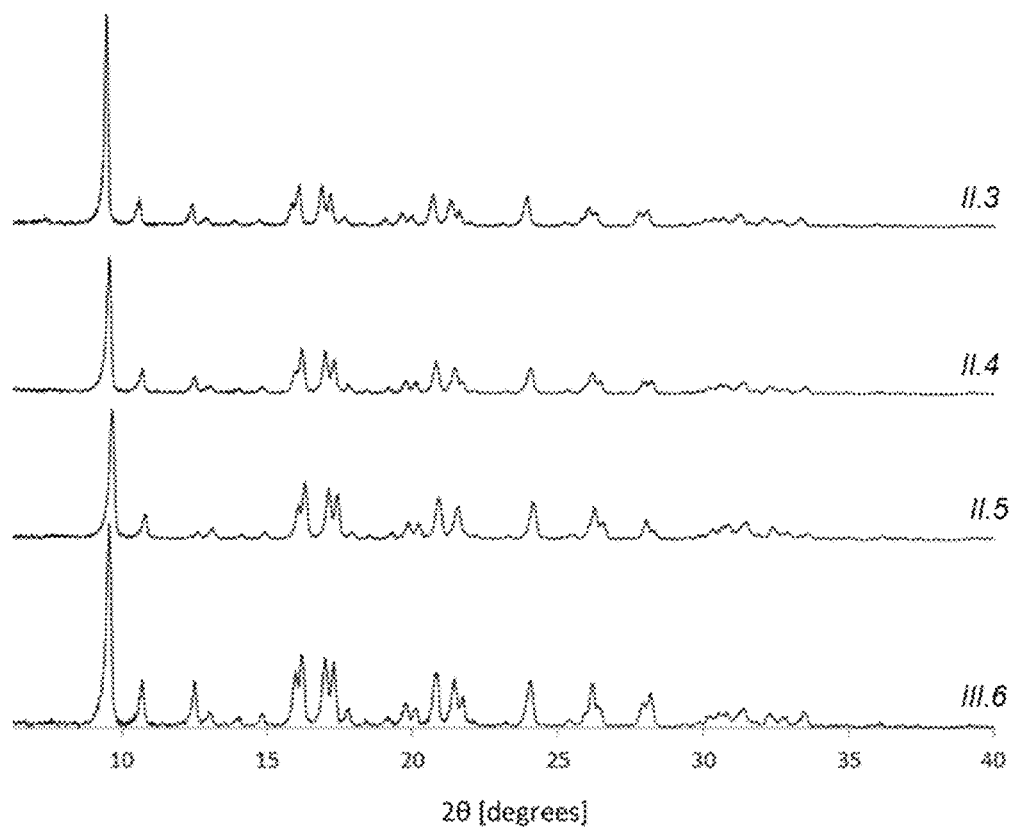
FIG. 12 shows PXRD powder XRD patterns of SSZ-39 made in conditions of Table II. entries 3, 4 and 5 and III.6.
Figure 17:
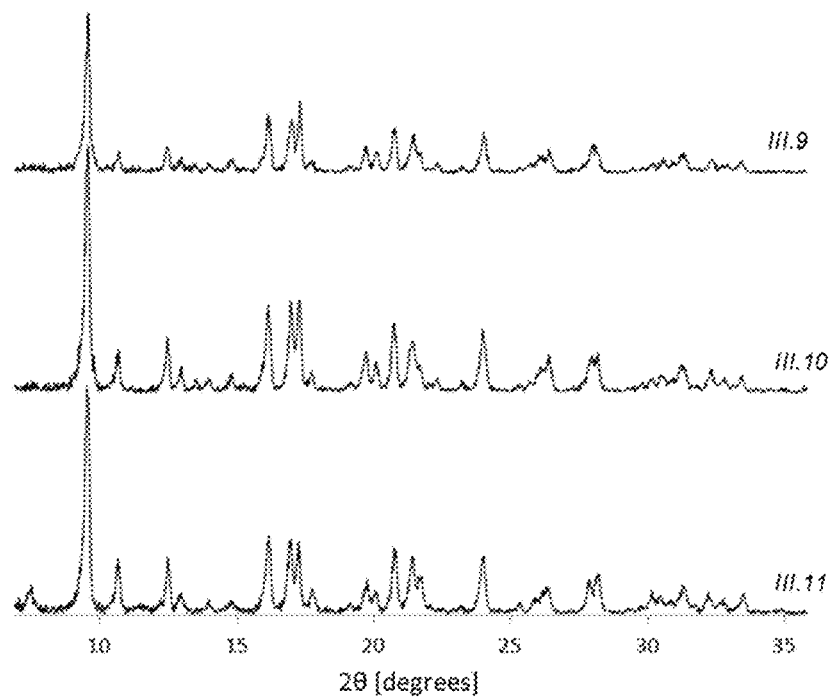
FIG. 17 shows additional powder XRD patterns of as-synthesized SSZ-39 made from Table II. Samples were made with different grades of cis-3,5/cis-2,6. The numbers correspond to Table III entries (III.9) 0/100 ratio; (III.10) 50/50; (III.11) 100/0.
Figure 18:
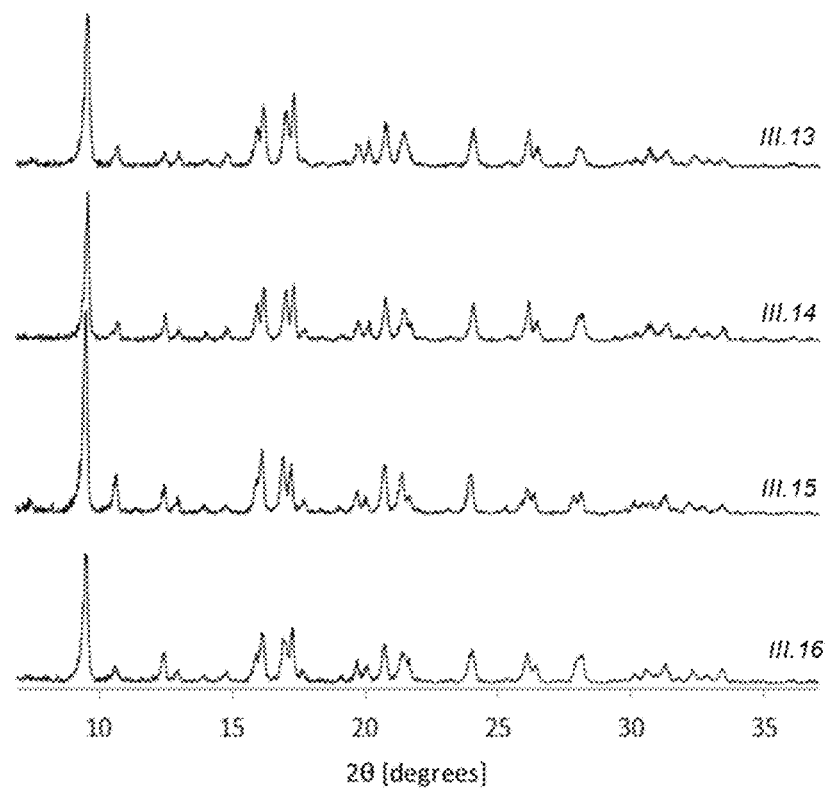
FIG. 18 shows additional powder XRD patterns of materials corresponding to entries in Table III. Entries 13 (cis-2,6); 14 (51/49 cis-3,5/cis-2,6); 12 (cis-3,5); 15 (24/26/50 cis-3,5/trans-3,5/cis-2,6).
Figure 19:
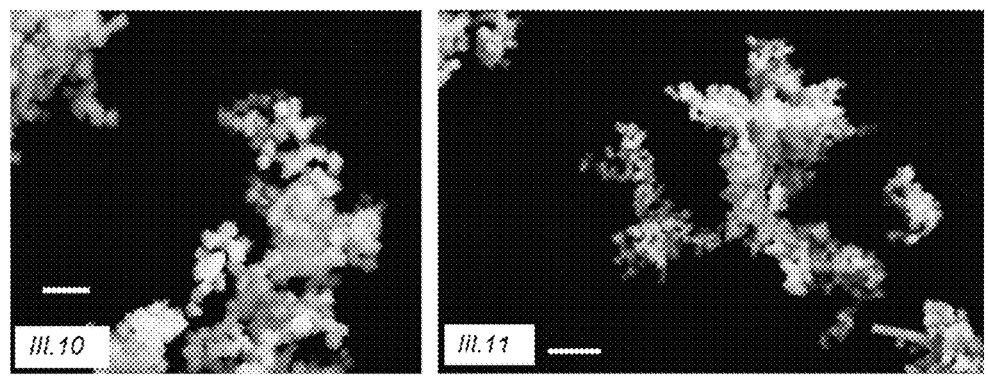
FIG. 19 shows additional SEM images of zeolites corresponding to Entries 13 and 14 of Table III.

To assess the influence of structural isomers of the lupetidine-based OSDAs and to aim at SSZ-39 synthesis using the nonselective synthesis of the lutidine precursor, the quaternized N,N-dimethyl-cis-2,6-lupetidine isomer was synthesized. The first set of syntheses (results listed in Table III entries 1-4) was conducted in gels with Si/Al ratios of 30 (same as the conditions of Table II, entries 1-2). Here, both the pure cis-2,6 isomer and the equimolar cis-3,5/cis-2,6 structural isomer mixture (entry 2) produced pure SSZ-39. The corresponding PXRD patterns are shown in FIG. 3, where they can be compared the products of pure cis-3,5 and diastereomer directed syntheses. Besides having identical diffraction patterns, the Si/Al ratios of the product SSZ-39 and the organic incorporation and yields were similar for all Si/Al=30 syntheses. To simulate an OSDA mixture derived from unselective lutidine production (e.g., equimolar in 2,6 and 3,5-isomer) followed by unselective hydrogenation (see FIGS. 2A-B), a mixture containing all 3 studied isomers in 24/26/50 ratios (cis-3,5/trans-3,5/cis-2,6) was tested. As seen by the data listed in Table III.4, this OSDA mixture produced a pure-phase SSZ-39. The syntheses in more Al-rich gels proved more difficult. The first pure cis-2,6 synthesis in a Si/Al=15 gel (Table III entry 5), was run at the conditions used for Table II, entries 3-5. It was clear that the cis-2,6 isomer was not selective for SSZ-39 in these conditions and led to MOR in the Al-rich gel (multiple trials). Therefore, two sets of modified conditions were identified where the cis-2,6 isomer could also lead to SSZ-39 in such gels. The first set (entries 9-11 in Table II), showed a composition with half the amount of OSDA as used before, but with additional NaOH to hold the total OH—:Si ratio constant at 0.65. Without hydroxide compensation, viz. entry 12, MOR started to dominate again. These gels were relatively low in OSDA, but still allowed SSZ-39 to form. The yield, as before, was mediocre, but the OSDA-efficiency—defined as the amount of OSDA in the SSZ-39 divided by the starting amount of OSDA in the gel—mounted up to about 30% (for Table III entry 11). This was higher compared to the efficiency calculated for Table II entry 3 (18%), where more OSDA per Si was used. The Si/Al ratios of the products of syntheses with 0.07 OSDA/Si ratio were a bit lower than before, likely because the influence of the organic (OSDA) over the inorganic (Na) charge-balancing cation was less significant. Concerning the produced phase, no significant differences were found in these conditions between both pure cis-lupetidine based OSDAs or their 50/50 mixture (Table III, entry 10). The corresponding PXRD patterns can be seen in FIG. 17. A second set of conditions for Si/Al=15 gels (Table III entries 13-16), was based on increasing the NaOH content of the gel slightly, up to NaOH/Si=0.54 (instead of 0.51 in Table II.3), while keeping the OSDA:Si ratio at 0.14. This adjustment was sufficient to keep the competing MOR phase in cis-2,6 directed syntheses (viz. Table III entry 5) from forming Again, in these sodium-rich syntheses, the use of either cis-3,5, cis-2,6 or mixtures thereof does not seem to influence the product, as the powder XRD patterns of the solids obtained were nearly identical (FIG. 18). The Si/Al ratio and the amount of OSDA in the SSZ-39 were similar as well, and the SEM images (FIG. 19) showed the same morphology as observed for the 3,5-isomeric mixtures (viz. FIG. 12). The disadvantage of these two sets of conditions for Al-rich gels (although they allowed a greater range of isomer mixtures in the OSDA, was the simultaneous growth of small amounts of GIS (and ANA). It should be noted that this influences the measured Si/Al ratio of the bulk products, e.g., 5.9 in entry III.15. Fortunately, the HCl treatment (FIG. 4) offers a straightforward solution to this problem.

TABLE III

Hydroxide Syntheses with Mixtures of cis- and trans-N,N-dimethyl-3,5-lupetidinium
Hydroxide Using Sodium Silicate as Silica and NH$_4$-FAU as alumina Sources

| | Gel composition relative to Si [a] | | | | | | | | | |
|---|---|---|---|---|---|---|---|---|---|---|
| Entry | Al | cis-3,5 | trans-3,5 | cis-2,6 | NaOH | cis-3,5/cis-2,6 [b] | Time, days | phase | Si/Al | TGA [d] (%) | Yield (%) |
| 1 | 0.033 | 0 | 0 | 0.140 | 0.57 | 0/100 | 3 | SSZ-39 | 9.5 | 20.6 | 23 |
| 2 | 0.033 | 0.069 | 0.001 | 0.070 | 0.57 | 50/50 | 3 | SSZ-39 | 8.7 | 19.3 | 27 |
| 3 [e] | 0.033 | 0.137 | 0.003 | 0 | 0.57 | 100/0 | 3 | SSZ-39 | 7.6 | 19.2 | 19 |
| 4 | 0.033 | 0.034 | 0.037 | 0.071 | 0.57 | 24/26/50 [c] | 3 | SSZ-39 | 9.3 | 19.3 | 23 |
| 5 | 0.067 | 0 | 0 | 0.140 | 0.51 | 0/100 | 3 | MOR | — | 7.8 | — |
| 6 | 0.066 | 0.128 | 0.003 | 0.008 | 0.51 | 94/6 | 6 | SSZ-39 [f] | — | 13.2 | 36 |
| 7 | 0.066 | 0.007 | <0.001 | 0.131 | 0.51 | 5/95 | 6 | MOR | — | — | — |
| 8 | 0.066 | 0.023 | <0.001 | 0.115 | 0.51 | 17/83 | 6 | MOR | — | — | — |
| 9 | 0.067 | 0 | 0 | 0.070 | 0.58 | 0/100 | 3 | SSZ-39 [f] | 5.2 | 12.6 | 32 [g] |
| 10 | 0.067 | 0.034 | <0.001 | 0.035 | 0.58 | 50/50 | 3.5 | SSZ-39 [f] | 5.0 | 12.7 | 38 |
| 11 | 0.067 | 0.071 | 0.001 | 0 | 0.58 | 100/0 | 3 | SSZ-39 [f] | 5.5 | 13.5 | 33 [g] |
| 12 | 0.067 | 0.071 | 0.001 | 0 | 0.51 | 100/0 | 3 | MOR | — | — | — |
| 13 | 0.067 | 0 | 0 | 0.142 | 0.54 | 0/100 | 3.7 | SSZ-39 [f] | 6.6 | 14.1 | 45 |
| 14 | 0.067 | 0.069 | 0.001 | 0.073 | 0.54 | 51/49 | 3.7 | SSZ-39 [f] | 6.5 | 11.9 | 42 |
| 15 | 0.067 | 0.137 | 0.03 | 0 | 0.54 | 100/0 | 3.7 | SSZ-39 [f] | 5.9 | 13.7 | 40 |
| 16 | 0.067 | 0.034 | 0.036 | 0.070 | 0.54 | 24/26/50 [c] | 3.7 | SSZ-39 [f] | 6.3 | 14.1 | 38 |

[a] H$_2$O:Si = 28 for all entries. NaOH:Si calculated from the total Na content, originating from NaOH addition and sodium silicate. Synthesis in a rotating oven at 140° C.
[b] Practical ratio of cis-3,5/cis-2,6 isomer. This neglects the small fraction of trans-3,5 isomer (2 mol %) present in the cis-3,5 isomer feedstock (see gel compositions)
[c] For entries 4 and 16, the cis-3,5/trans-3,5/cis-2,6 isomer is given.
[d] Weight % loss in TGA between 300° C. and 900° C. relative to the amount of zeolite left at 900° C.
[e] Same synthesis as in Table II. 1
[f] GIS/ANA impurities noticed in these samples; see FIGS. 17 and 18.
[g] Yields after 5 days, but PXRD patterns after 3 and 5 days was identical and absent of starting FAU.

Figure 7:
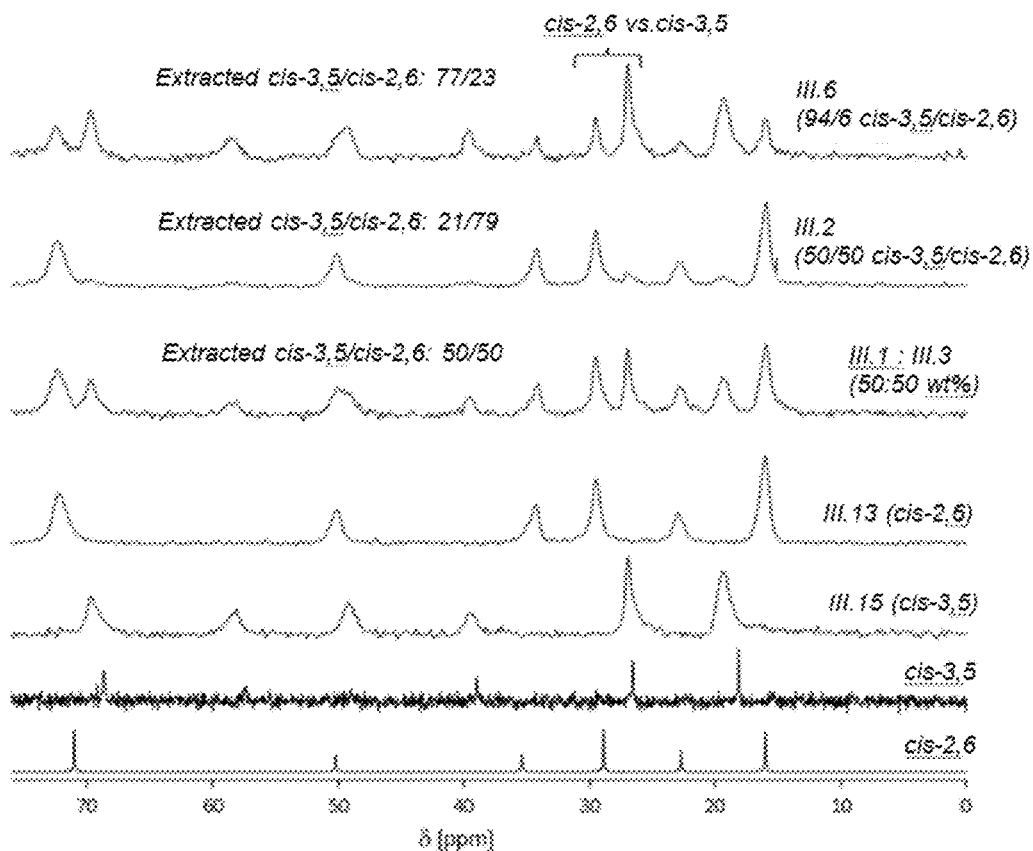
FIG. 7 shows $^{13}$C CP-MAS NMR of cis-3,5 and cis-2,6 standards compared to as synthesized SSZ-39 made with different grades of cis-3,5/cis-2,6. The numbers correspond to Table III entries. (III.15) cis-3,5; (III.13) cis-2,6; physical mixture (50:50 wt %) of III.1 (cis-2,6) and III.3 (cis-3,5); (III.2) 50/50; (III.6) 94/6. The extracted ratios are measured by $^1$H-NMR after SSZ-39 dissolution.

Similar to the cis/trans-3,5 differentiation that is illustrated by the data shown in FIG. 5, it was possible to detect different resonances belonging to either the cis-3,5 and/or cis-2,6 isomers in $^{13}$C CP-MAS NMR analyses (FIG. 7) Products of pure cis-3,5 and cis-2,6 directed syntheses nicely matched up with their respective standards. As a second control, a 1:1 (weight-based) physical mixture of two pure SSZ-39 made with the cis-2,6 (Table III.1) and cis-3,5 isomer (Table III.3) was assessed. As seen in the data shown in FIG. 7, the intensities of the 27 and 30 ppm signal were near 1:1 for this trace. In the SSZ-39 synthesized with a 50/50 cis-3,5/cis-2,6 mixture (Entry II.2), however, the cis-2,6 isomer seemed preferentially present in CP-MAS-NMR. This was confirmed by the results from the SSZ-39 dissolution and OSDA extraction protocol that yielded a 21/79 cis-3,5/cis-2,6 distribution (listed above the NMR traces in FIG. 7). Identical NMR data were obtained for other SSZ-39 produced in the 50/50 gels (Si/Al 15, Table III.10 and III.14).

Figure 20:
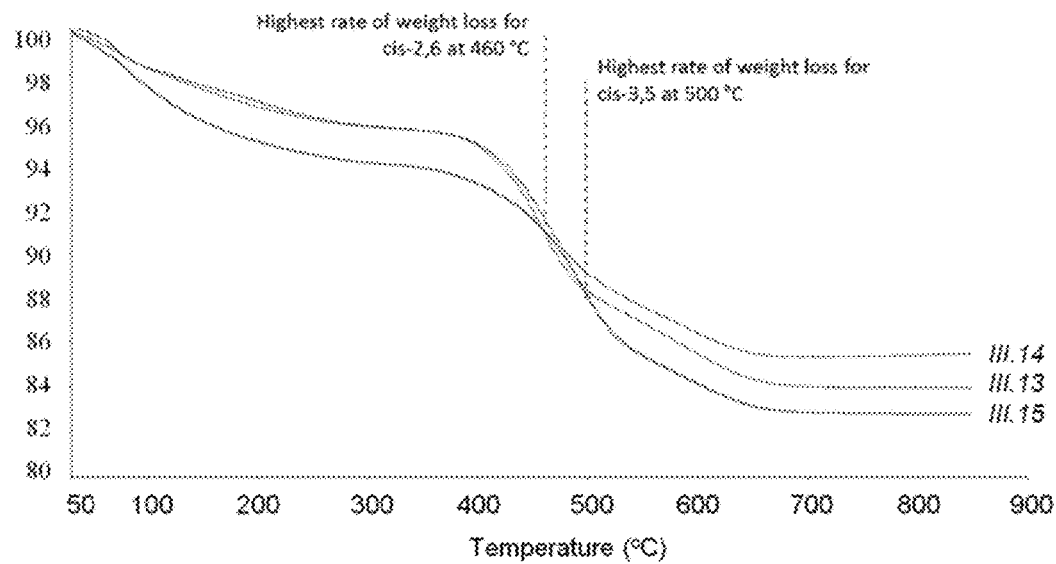
FIG. 20 shows additional TGA corresponding to Entries 13, 14 and 15 of Table III. Note how the weight loss of the zeolite made with the 50/50 cis/cis gel (III.14) displays a similar weight loss profile as the zeolite made with pure cis-2,6 (III.13), with maximum weight loss at 460° C. The cis-3,5 isomer leads to a profile with maximum weight loss at 500° C. (III.15). TGA thus corroborated the MAS NMR data that showed that zeolites made in 50/50 mixtures preferentially incorporate cis-2,6. The end point of the TGA analysis is dependent on the total organic and moisture weight loss.
Figure 21:
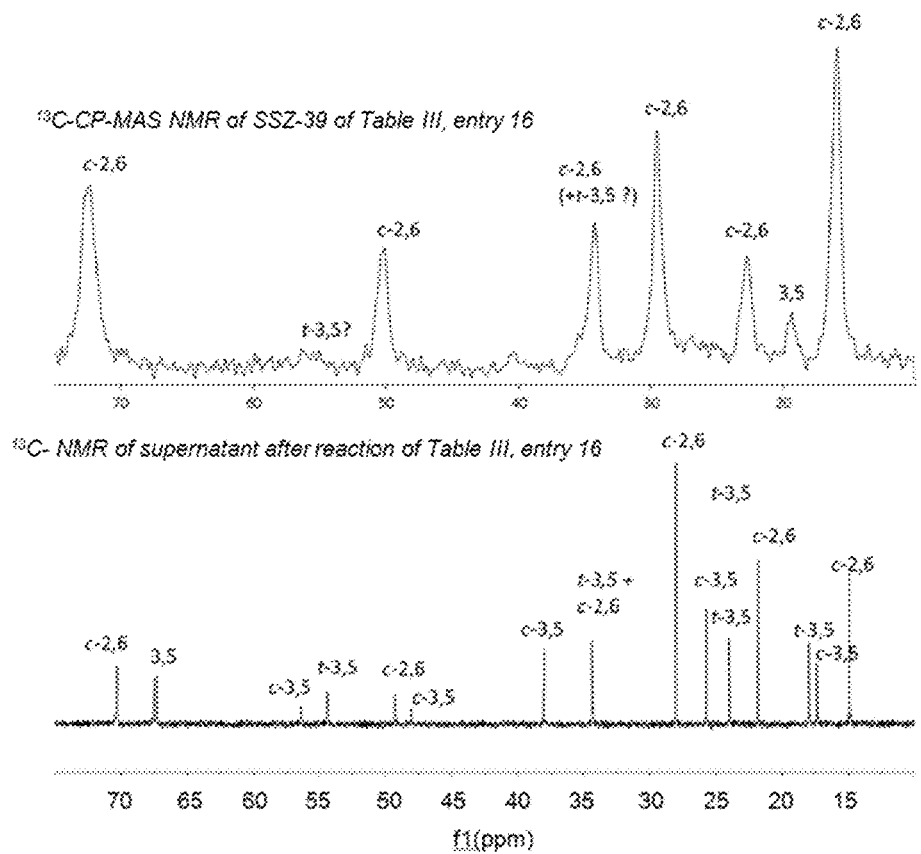
FIG. 21 shows results of a supernatant liquid phase NMR and zeolite MAS NMR study for the synthesis of Table III.16. Reaction carried out as seen in main manuscript Table III, entry 16. This reaction started with a 24/26/50 cis-3,5/trans-3,5/cis-2,6 ratio. After reaction, the $^1$H-NMR of the supernatant pointed to a distribution of 28.3/28.3/43.3. Based on the total amount of OSDA taken up in the SSZ-39 as analyzed by TGA (14.1%), the stereospecific uptake in the zeolite could be calculated and pointed to a 3.9/15.8/80.8 distribution. The CP-MAS NMR spectra in FIG. 16 confirms that the cis-2,6 was again taken up in excess. Some signals belonging to the 3,5 isomer could be picked up. Interestingly, the zeolite should have taken up more trans- than cis-3,5 according to the calculation. In the non-quantitative CP MAS NMR this was hard to verify. Therefore, the SSZ-39 was dissolved in 50 wt % HF according to the procedure outlined below. After drying, the organic content was extracted in CDCl$_3$ and analyzed by $^1$H-NMR. The analysis rendered a 12/24/64 distribution, indeed confirming the preferential incorporation of the 2,6 over the 3,5-isomer and that the trans- over the cis-3,5 isomer and in the same order as in the calculated distribution based on supernatant and TGA.

These analyses point to an intriguing contrast: although the cis-2,6 isomer was not able to direct to SSZ-39 in all conditions (exemplified by the MOR synthesis in entry III.5), it was preferentially incorporated if present in equimolar amounts with the 3,5-isomer in the optimal SSZ-39 producing conditions. This preferential incorporation was confirmed by TGA analysis (FIG. 20), by observing the temperature where the maximum organic removal occurred in the weight-loss profile. The profiles of 50:50 and pure cis-2,6 directed SSZ-39 were very similar and in contrast with the cis-3,5 combustion profile. To further explore this phenomenon, 2 additional syntheses were run at conditions where the cis-2,6 isomer proved unable to produce SSZ-39 (conditions of Table III.5 or II.3-4): one with a 94/6 cis-3,5/cis-2,6 mixture and one with a 5/95 mixture, respectively (entries 6 and 7 in Table III). If successful toward synthesizing SSZ-39, the latter mixture could hint to the role of the cis-3,5 isomer as the better initiating and nucleating agent, followed by the easier incorporation of cis-2,6 isomer in the following growth phase. However, this synthesis produced MOR as the major phase, with only trace SSZ-39. The reverse experiment, with a 94/6 ratio, led to SSZ-39 (+GIS) absent of MOR (PXRD trace in FIG. 12). Interestingly, $^{13}$C CP-MAS NMR, shown as the upper curve in FIG. 7, as well the OSDA extraction pointed to an isomer distribution of 77/23 in the SSZ-39. These data indicated that nearly ⅓ of the occluded organic consisted of the cis-2,6 isomer, even though its initial abundance in the gel was only 6%. The OSDA efficiency here, calculated by combining NMR and TGA information, amounts to ±67% for the cis-2,6 and only ±12% for the cis-3,5 isomer. An additional control experiment (isomeric mixture of 17/83, Table III.8) also failed to produce SSZ-39. Lastly, the kinetics of SSZ-39 formation in Si/Al=30 gels with the cis-2,6 isomer was assessed in analogy with the earlier 3,5-isomer kinetics. As seen in the data shown in FIG. 6, the cis-2,6 directed synthesis proceeded at a lower rate than the cis-3,5 and 48/52 cis/trans-3,5 mixture. This confirmed that the 3,5-lupetidine based OSDA (and even more so the trans-3,5 isomer) was a better initiator than the cis-2,6-lupetidine based OSDA. In conditions where MOR formation was unfavorable, all isomeric mixtures led to SSZ-39, with a relative rate-of-formation order as follows: trans-3,5>cis-3,5>cis-2,6. When presented in competition, a preferential incorporation of trans-3,5 over cis-3,5 and cis-2,6 over cis-3,5 ensues. Further confirmation of this was found in the syntheses of entries 4 and 16 in Table III, which respectively displayed 10/21/69 and 12/24/64 ratios in SSZ-39 zeolites produced in 24/26/50 cis-3,5/trans-3,5/cis-2,6 gels (explained in depth in FIG. 21).

In summary, structure direction appears to be governed by a complex interplay between the hydroxide content, both organic and inorganic cations, the starting FAU zeolite Al-source and competing phases.

Example 4

Characterization of SSZ-39 Samples

Figure 8A:
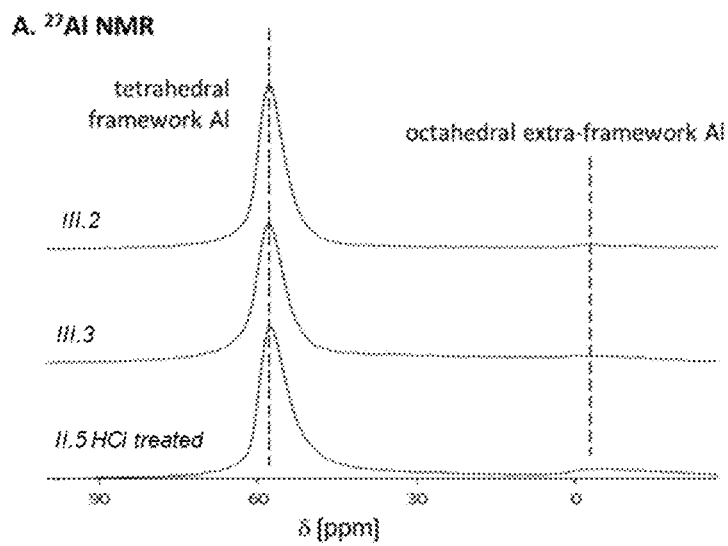
FIG. 8A shows $^{27}$Al MAS NMR of calcined SSZ-39 made with different isomer OSDA mixtures. The numbers correspond to the entries in Tables II and III.
Figure 8B:
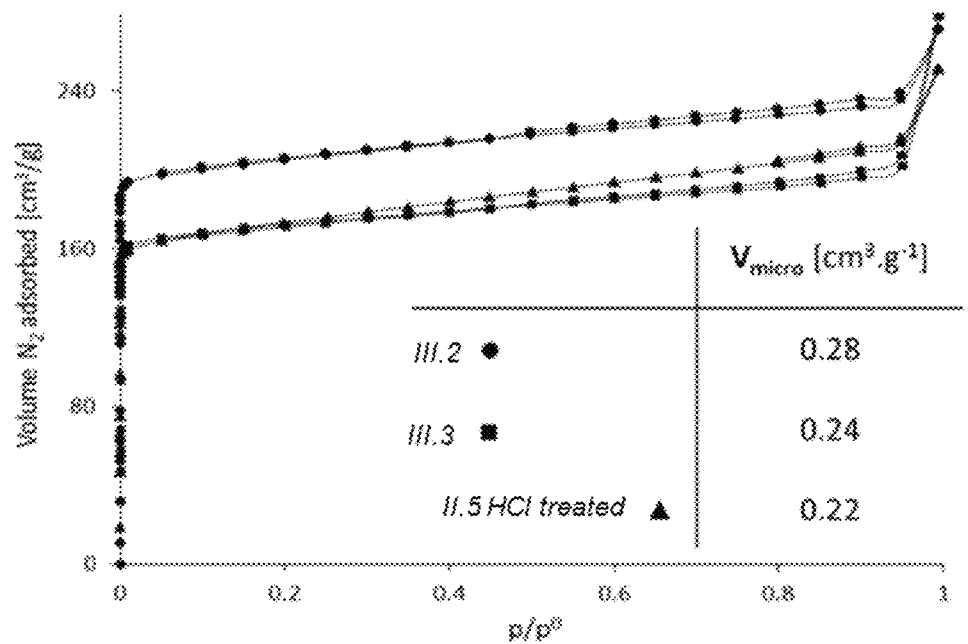
FIG. 8B shows $N_2$-physisorption isotherms and micropore volume from t-plot analyses ($H^+$-form).
Figure 9:
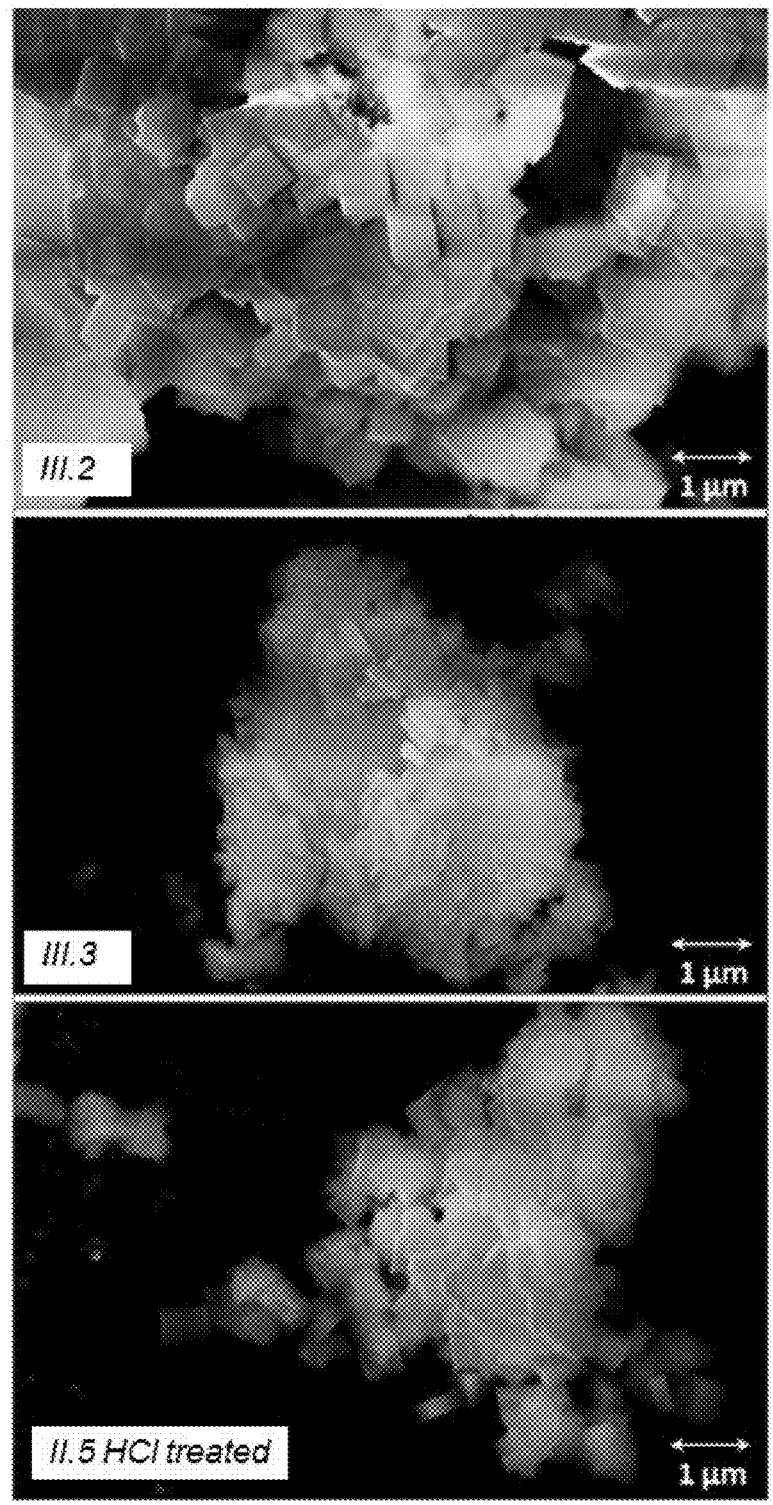
FIG. 9 shows SEM images of compositions III.2, III.3, and HCl treated 11.5 at a magnification of 40,000

Three SSZ-39 samples made with different OSDA mixtures and/or gel recipes were selected for characterization. After calcination for removal of the organic, $^{27}$Al MAS NMR and full elemental analysis was performed, as well as SEM for analyzing the crystallite morphologies. Additionally, after $NH_4^+$-exchange and calcination, the microporosity of the H—SSZ-39 solid was analyzed. FIGS. 8A-B, 9 and Table III display an overview of these results. The pure SSZ-39 obtained from Si/Al=30 gels of Table III (entries 2 and 3) were selected for study, as the latter represents a pure cis-3,5 synthesis, while the former was derived from a mixed structural isomer synthesis, but with preferential cis-2,6 incorporation. The third sample assessed was the acid-treated version from Table I, entry 5 (FIG. 4), derived from a mixed diastereo-isomer (50/50 cis/trans-35) synthesis with preferred trans uptake in a Si/Al=15 gel.

The Al NMR traces in FIG. 8A with dominating bands at 57 ppm showed that nearly all of the aluminum was incorporated tetrahedrally into the framework. The elemental analyses in Table IV confirmed the Si/Al ratios as measured by EDS. The Na/Al ratios were around 0.3 for both entries IV.2 and IV.3, but much lower for the acid washed material. This was caused by the HCl-mediated exchange of some of the Na cations for $H^+$. The presence of Na cations in the calcined SSZ-39 explained the slightly lower Si/Al ratios than what theoretically could be expected for a complete filling of each cage with one OSDA. The Si/Al values for samples IV.2 and IV.3 respectively led to 4.8 and 5.4 Al atoms per unit cell. This tetrahedral Al (viz. $^{27}$Al NMR) should have induced an equimolar amount of negative framework charge and was compensated by a maximum of 4 positively charged SDAs (in 4 cages) per unit cell. Combining TGA and elemental analysis, 3.9 OSDAs per unit cell were calculated for both materials. The charge deficit (viz. −0.9 and −1.5) was thus roughly accounted for by the presence of respectively 1.3 and 1.75 $Na^+$ per unit cell for III.2 and III.3 as measured by elemental analysis. The micropore volumes (FIG. 8B) seem to differ to some extent, with the lowest value obtained for the acid-washed material (0.22 cc/g). This could have originated from the slightly higher Al content of this material. Generally, the pore volumes (and type of isotherm) were within the expected range for a highly crystalline microporous 3-dimensional 8MR molecular sieve with cages, and in line with SSZ-39 literature.

TABLE IV

Full elemental analysis after calcination

| Sample | Na | Si | Al | Si/Al |
|---|---|---|---|---|
| II.2 | 1.1 | 4.0 | 36.9 | 9.1 |
| II.3 | 1.5 | 4.6 | 36.3 | 7.9 |
| I.5. Hcl treated | 0.7 | 5.2 | 37.8 | 7.2 |

Figure 22:
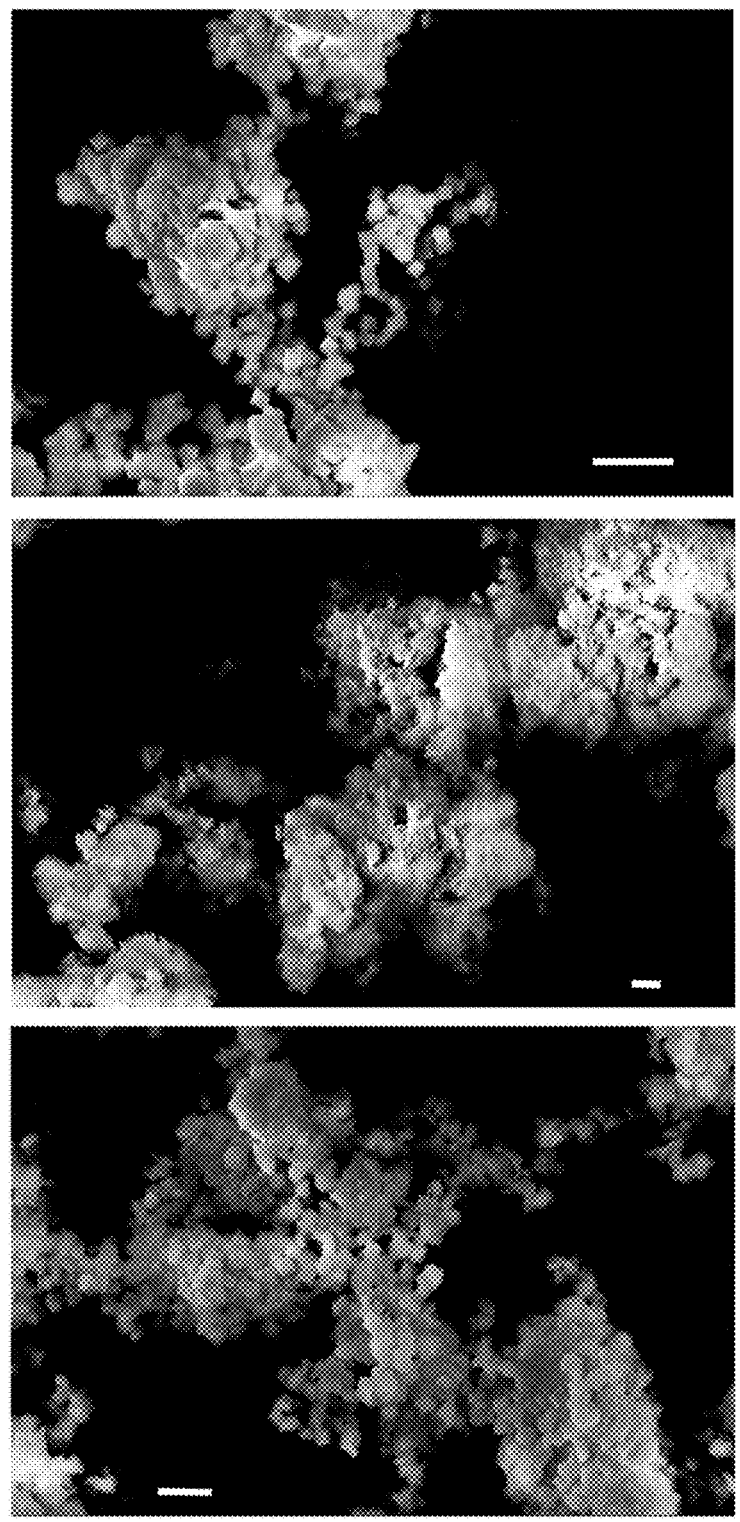
FIG. 22 shows additional SEM images of SSZ-39 in main manuscript FIG. 6
Figure 23:
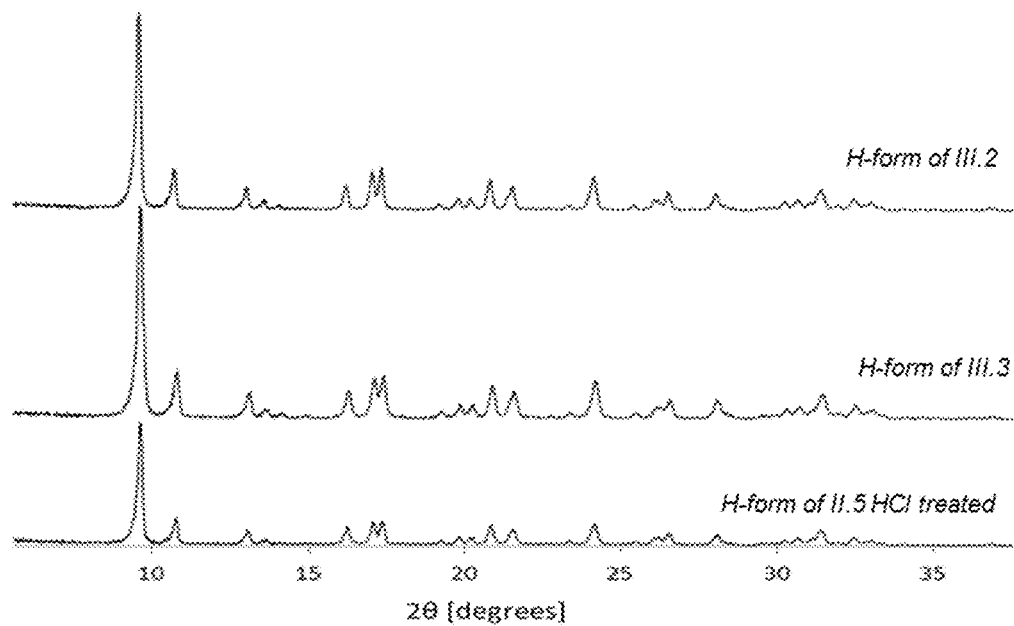
FIG. 23 shows powder XRD patterns of $H^+$—SSZ-39 of FIG. 6 (Table III.2 and III.3 and Table II.5 HCl treated). These SSZ-39 are the ones on which the pore volume physisorption experiments have been run. They have been calcined, exchanged three times with 1M NH$_4$NO$_3$ solutions (1 g/100 mL, 2 h at 90° C.) and calcined again. These PXRD profiles contain all the reflections matching calcined SSZ-39 as reported by Moliner and Zones et al.

Finally, the crystal morphologies of all calcined materials (FIG. 9), were similar (square-rectangular) and size in the range of 0.5-1 μm, although the material made with pure cis-3,5 was slightly smaller (III.3). Additional SEM images and powder XRD patterns of the $H^+$-form materials are shown in FIG. 22 and FIG. 23. From these characterizations, it was concluded that all SSZ-39 samples, although prepared with different isomer mixtures, are typical SSZ-39 materials.

As those skilled in the art will appreciate, numerous modifications and variations of the present invention are possible in light of these teachings, and all such are contemplated hereby. For example, in addition to the embodiments described herein, the present invention contemplates and claims those inventions resulting from the combination of features of the invention cited herein and those of the cited prior art references which complement the features of the present invention. Similarly, it will be appreciated that any described material, feature, or article may be used in combination with any other material, feature, or article, and such combinations are considered within the scope of this invention.

The disclosures of each patent, patent application, and publication cited or described in this document are hereby incorporated herein by reference, each in its entirety, for all purposes The following references may be useful in understanding the background and certain aspects of the present invention:

1. IZA-Structure-Commission, *Database of Zeolite Structures* http://izasc.biw.kuleuven.be/fmi/xsl/IZA-SC/ft.xsl, Accessed 23 Jan. 2015.
2. (a) Zones, S. I.; Nakagawa, Y.; Evans, S. T.; Lee, G. S. Zeolite SSZ-39. U.S. Pat. No. 5,958,370, 1999; (b) Cao, G.; Strohmaier, K. G.; Li, H.; Guram, A. S.; Saxton, R. J.; Muraoka, M. T.; Yoder, J. C.; Yaccatu, K. Synthesis of AEI-type zeolites and their use in the conversion of oxygenates to olefins. WO2005063624 A1, 2005.
3. Moliner, M.; Franch, C.; Palomares, E.; Grill, M.; Corma, A., Cu—SSZ-39, an active and hydrothermally stable catalyst for the selective catalytic reduction of NOx. *Chem. Commun.* 2012, 48 (66), 8264-8266.

What is claimed:

1. A process of preparing a microporous crystalline aluminosilicate composition having an SSZ-39 framework topology, the process comprising hydrothermally treating an aqueous composition under conditions to crystallize the microporous crystalline composition having the SSZ-39 framework topology, the aqueous composition comprising:
   (a) at least one source of silicon oxide and optionally at least one source of germanium oxide, or a combination thereof;
   (b) at least one source of aluminum oxide;
   (c) water; and
   (d) an organic structure directing agent consisting essentially of trans-N,N-dialkyl-3,5-lupetidinium cations and one or both of cis-N,N-dialkyl-3,5-lupetidinium or cis-N,N-dialkyl -2,6-lupetidinium cations, wherein the molar ratio of trans-N,N-dialkyl-3,5-lupetidinium cation to the cis-lupetidinium cations is in a range of from 40:60 to 90:10.

2. The process of claim 1, wherein the composition further comprises at least one source of germanium oxide, boron oxide, gallium oxide, hafnium oxide, iron oxide, tin oxide, titanium oxide, indium oxide, vanadium oxide, zirconium oxide, or a combination thereof.

3. The process of claim 2, wherein the source of boron oxide, gallium oxide, germanium oxide, hafnium oxide, iron oxide, tin oxide, titanium oxide, indium oxide, vanadium oxide, zirconium oxide, or combination or mixture thereof comprises an alkoxide, hydroxide, oxide, or combination thereof of the corresponding metal.

4. The process of claim 1 wherein the structure directing agent consists essentially of a trans-N,N-dimethyl-3,5-lupetidinium cation and one or both of cis-N,N-dimethyl-3,5-lupetidinium or cis-N,N-dimethyl-2,6-lupetidinium cations.

5. The process of claim 1, wherein the organic structure directing agent consists of trans-N,N-dialkyl-3,5-lupetidinium cations and one or both of cis-N,N-dialkyl-3,5-lupetidinium or cis-N,N-dialkyl-2,6-lupetidinium cations, wherein the molar ratio of trans-N,N-dialkyl-3,5-lupetidinium cation to the cis-lupetidinium cations is in a range of from 40:60 to 90:10.

6. The process of claim 1, wherein the structure directing agent consists essentially of a trans-N,N-diethyl-3,5-lupetidinium cation and one or both of cis-N,N-diethyl-3,5-lupetidinium or cis-N,N-diethyl -2,6-lupetidinium cations.

7. The process of claim 1, wherein the organic structure directing agent consists essentially of a mixture of cis-N,N-dimethyl-2,6-lupetidinium cation and trans-N,N-dimethyl-3,5-lupetidinium cation in a molar ratio of about 50% cis/50% trans to about 20% cis/80% trans.

8. The process of claim 1, wherein the organic structure directing agent consists essentially of a mixture of cis-N,N-dimethyl-3,5-lupetidinium cation and trans-N,N-dimethyl-3,5-lupetidinium cation in a molar ratio of about 50% cis/50% trans to about 25% cis/75% trans.

9. The process of claim 1 or 5, wherein the organic structure directing agent mixture comprises a bromide, chloride, fluoride, iodide, or hydroxide salt.

10. The process of any one of claim 1 or 5, wherein the source of silicon oxide comprises a silicate, silica hydrogel, silicic acid, fumed silica, colloidal silica, tetra-alkyl orthosilicate, a silica hydroxide or combination thereof.

11. The process of claim 1 or 5, wherein the source of aluminum oxide comprises an alkoxide, hydroxide, or oxide of aluminum, a sodium aluminate, an aluminum siloxide, an aluminosilicate, or combination thereof.

12. The process of claim 1, wherein the mole ratio of Si:Al in the composition is in a range of from about 5:1 to about 250:1.

13. The process of claim 1 or 5, wherein the mole ratio of water to Si is in a range of from about 2:1 to about 50:1.

14. The process of claim 1 or 5, wherein the mole ratio of the structure directing agent to Si is in a range of from about 0.01:1 to about 1:1.

15. The process of claim 1 or 5, wherein the composition to be hydrotreated further comprises aqueous hydroxide.

16. The process of claim 15, wherein the mole ratio of hydroxide to Si in the composition is in a range of from about 0.5:1 to about 1:1.

17. The process of claim 1 or 5, wherein the hydrothermal treating is done at a temperature in a range of from about 100° C. to about 200° C.

18. The process of claim 1 or 5, further comprising isolating the crystalline microporous solid.

19. The process of claim 1 or 5, further comprising calcining the crystalline microporous solid at a temperature in a range of from about 350° C. to about 850° C.

20. The process of claim 19, further comprising treating the calcined material with an aqueous ammonium salt.

21. The process of claim 19, further comprising treating the calcined crystalline microporous solid with at least one alkaline earth metal or alkaline earth metal oxide, transition metal or transition metal oxide.

22. The process of claim 1 or 5, wherein the trans-N,N-dialkyl-3,5-lupetidinium cation is trans-N,N-dimethyl-3,5-lupetidinium cation.

23. The process of claim 5, wherein the structure directing agent consists of a trans-N,N-diethyl-3,5-lupetidinium cation and one or both of cis-N,N-diethyl-3,5-lupetidinium or cis-N,N-diethyl-2,6-lupetidinium cations.

24. The process of claim 5, wherein the organic structure directing agent consists of a mixture of cis-N,N-dimethyl-2,6-lupetidinium cation and trans-N,N-dimethyl-3,5-lupetidinium cation in a molar ratio of about 50% cis/50% trans to about 20% cis/80% trans.

25. The process of claim 5, wherein the organic structure directing agent consists of a mixture of cis-N,N-dimethyl-3,5-lupetidinium cation and trans-N,N-dimethyl-3,5-lupetidinium cation in a molar ratio of about 50% cis/50% trans to about 25% cis/75% trans.

* * * * *